US007348012B2

(12) United States Patent
Davelaar

(10) Patent No.: US 7,348,012 B2
(45) Date of Patent: Mar. 25, 2008

(54) METHODS AND VACCINES FOR PROVIDING IN OVO PROTECTION AGAINST TURKEY RHINOTRACHEITIS

(75) Inventor: Frans Gerrit Davelaar, Putten (NL)

(73) Assignee: Wyeth, Madison, NJ (US)

( * ) Notice: Subject to any disclaimer, the term of this patent is extended or adjusted under 35 U.S.C. 154(b) by 45 days.

(21) Appl. No.: 11/251,692

(22) Filed: Oct. 17, 2005

(65) Prior Publication Data

US 2006/0034868 A1 Feb. 16, 2006

Related U.S. Application Data

(63) Continuation of application No. 10/054,288, filed on Nov. 13, 2001, now abandoned.

(60) Provisional application No. 60/252,162, filed on Nov. 21, 2000.

(51) Int. Cl.
*A61K 39/12* (2006.01)

(52) U.S. Cl. .................................................... 424/204.1

(58) Field of Classification Search ............... 424/93.2, 424/93.6

See application file for complete search history.

(56) References Cited

U.S. PATENT DOCUMENTS

| | | | | |
|---|---|---|---|---|
| 4,458,630 | A * | 7/1984 | Sharma et al. | 119/6.8 |
| 5,069,902 | A * | 12/1991 | Cook et al. | 424/211.1 |
| 5,187,087 | A | 2/1993 | Sondermeijer et al. | |
| 5,470,734 | A | 11/1995 | Sondermeijer et al. | |
| 5,925,358 | A | 7/1999 | Cochran et al. | |
| 6,001,369 | A | 12/1999 | Cochran et al. | |
| 6,033,670 | A | 3/2000 | Bublot et al. | |
| 6,136,318 | A | 10/2000 | Cochran et al. | |
| 6,153,199 | A | 11/2000 | Audonnet et al. | |
| 6,221,361 | B1 | 4/2001 | Cochran et al. | |
| 6,221,362 | B1 | 4/2001 | Audonnet et al. | |
| 6,306,400 | B1 | 10/2001 | Bublot et al. | |

FOREIGN PATENT DOCUMENTS

| | | |
|---|---|---|
| WO | WO 98/26800 | 6/1998 |
| WO | WO 99/53950 | 10/1999 |
| WO | WO 01/64244 A2 | 9/2001 |

OTHER PUBLICATIONS

Worthington et al. Immunity to TRT in turkeys following in ovo vaccination. In HM Hafez (ed) 3rd International Symposium on Turkey Diseases, German Veterinary Medical Society, Berlin, Jun. 14-17, 2000, pp. 249-255.*

The Proceedings from the 3rd International Symposium on Turkey Diseases [online]. German Veterinary Medical Society, 2000 [retrieved on Sep. 19, 2007]. Retrieved from the Internet <URL:www.poultry-health.com/fora/turkhelth/symp3.htm>.*

C. A. Ricks et al., "In Ovo Vaccination Technology," Advances in Veterinary Medicine, 1999, pp. 495-515, vol. 41, Academic Press.

J.K.A. Cook, "Avian rhinotracheitis," Rev. Sci. Tech. Off. Int. Epiz., 2000, pp. 602-613, vol. 19(2), Intervet UK Ltd., The Elms.

* cited by examiner

*Primary Examiner*—Bruce Campell
*Assistant Examiner*—Louise Humphrey
(74) *Attorney, Agent, or Firm*—Frank R. Cottingham

(57) ABSTRACT

Methods and compositions for protecting avian hosts (e.g., turkeys and/or chickens) from turkey rhinotracheitis virus and/or TRT or SHS respiratory distress utilize in ovo administration of live, avirulent strains of TRTV at appropriate dosage levels on a per egg basis to provide an effective and efficient vaccination having acceptable safety and efficacy features, and additionally provides higher titers in vaccinated birds than conventionally administered vaccines.

9 Claims, No Drawings

METHODS AND VACCINES FOR PROVIDING IN OVO PROTECTION AGAINST TURKEY RHINOTRACHEITIS

Cross-Reference to Related U.S. Applications

This application is a continuation application of co-pending Nonprovisional Application No. 10/054285 filed on Nov. 13, 2001, now abandoned which claims the priority benefit under 35 U.S.C. § 119(e) of U.S. Provisional Application No. 60/252,162, filed on Nov. 21, 2000, abandoned, the entire disclosure of which is hereby incorporated by reference.

FIELD OF THE INVENTIONS

The invention is directed to useful methods for providing in ovo protection against turkey rhinotracheitis (TRT) and/or "Swollen Head Syndrome" (SHS) in avian hosts such as turkeys and chickens. More particularly, vaccines against TRT have proven to be both safe and efficacious upon appropriate in ovo administration to avian hosts as described herein.

BACKGROUND OF THE INVENTION

TRT is an upper respiratory tract infection of turkeys that is caused by pneumovirus. It is a highly contagious, acute disease that afflicts turkeys of all ages. The clinical symptoms of TRT infection include a marked, frequently frothy nasal discharge, rales, snicking, sneezing, and head shaking. Ocular discharge or swollen infraorbital sinuses may also be observed in infected turkeys.

Antibodies to TRT virus (TRTV) have been detected in some chicken flocks (both broilers and broilers/breeders) suffering from Swollen Head Syndrome (SHS). It is postulated that TRTV plays a role in the etiology of SHS and related respiratory distress.

Commercially-available vaccines for TRT are not administered in ovo. Rather, they are administered post-hatch in a variety of formats. Typically, such vaccines are administered by the labor-intensive methods of spraying (e.g., hand spray, knapsack spray, or automated-spray equipment) or in drops (eye or nose).

As more fully explained below, the in ovo administration methods of using TRT vaccines modified for in ovo use provides distinctive advantages over the inconvenient and time-consuming post-hatch routes of administration presently available.

SUMMARY OF THE INVENTION

The present invention utilizes commercially-available TRT vaccines adapted for the in ovo methods of administration of the present invention. Experimental results establish the safety and efficacy of the in ovo administration of these vaccines to turkeys and to chickens using appropriate dosing parameters.

The methods of the present invention can be utilized to protect an avian host against TRT, and/or TRT or SHS-related respiratory distress by in ovo administration of such vaccines.

It is thus an object of the present invention to provide a method of protection avian hosts from TRT and/or TRT or SHS-related respiratory distress using in ovo vaccination techniques which are easier and less expensive to apply to large populations of birds.

It is further an object of the present invention to provide such in ovo vaccination using vaccines in dosages which provide a suitable immunological response in hatched avian hosts without adversely affecting hatch rates.

It is a still further object of this invention to provide protection against SHS-related respiratory distress using TRT vaccines adapted for in ovo administration.

It is yet another object of the present invention to provide a method of vaccinating avian hosts against TRT and/or TRT or SHS-respiratory distress which provides elevated titers to TRTV as compared to conventionally vaccinated birds, using lesser amounts of vaccine antigen, thus resulting in cost savings.

DETAILED DESCRIPTION OF THE INVENTION

The present invention provides a method for immunizing in ovo avian hosts against TRTV, and thus providing protection against TRT and/or TRT and SHS respiratory distress. The vaccines utilized in the methods of the present invention can advantageously be prepared from commercially-available TRT vaccines. Especially suitable for use in the present invention is the commercially available Poulvac® TRT vaccine, available from Fort Dodge Animal Health, Fort Dodge, Iowa or Weesp, The Netherlands. The commercial formulation of Poulvac® TRT contains attenuated TRTV, strain K, with a titer of not less than $10^{3.2}$ $TCID_{50}$ per dose and is not approved or indicated for in ovo administration. Throughout this application, "$TCID_{50}$" refers to a 50% tissue culture infectious dose.

Typically, the vaccine is resuspended in a suitable vehicle so as to provide a TCID50 in the range of about $10^{3.2}$ to about $10^{4.5}$, and administered in an amount of approximately 0.05 to 0.1 ml per egg, depending upon the avian species being immunized. Administration may be by hand, but is more typically and economically administered by using commercially available egg injection equipment such as that available from Embrex, Inc., North Carolina. The exact dosage to be administered will depend upon the avian species to which the vaccine is to be delivered, e.g., smaller birds will require smaller doses. Administration of the vaccine typically occurs on or before day 24 of incubation (e.g., turkeys), but other in ovo vaccination times are within the scope of the invention, for example, on or before day 18 of incubation (e.g., chickens).

Avian hosts for which the vaccines and methods of the present invention are intended include chickens, ducks, turkeys, geese, bantams, quail and pigeons. Preferred avian species are the commercially important poultry birds such as chickens, ducks and turkeys.

It has surprisingly been found that not only is the in ovo method of vaccination safe and easier to administer, but that higher titers are found in avian hosts which have been immunized in this manner.

In addition, the vaccine and method of administration result in substantially no decrease in the percentage of eggs that hatch after in ovo vaccination, when compared to a substantially identical control (non-vaccinated) group. Preferably, this decrease is less than about 10%, and more preferably is less than about 5% relative to the percentage that hatch in the control group. Even more desirable is a decrease of less than about 1-2%. In some embodiments, the vaccine and method of the invention may actually increase the percentage of eggs that hatch, sometimes by as much as about 1-2% or even more. Thus, the vaccine is both safe and effective for administration to avian species such as chickens and turkeys.

The following examples describe in detail the methods and techniques illustrative of the present invention. It will be apparent to those skilled in the art that many modifications, both of materials and methods, may be practiced without departing from the purpose and intent of this disclosure.

EXAMPLES

Example 1

Safety Study for in ovo Turkey Administration

Fertile turkey eggs for hatching were obtained from parent turkey flocks which were known to be free of TRTV; and which had not been previously vaccinated against TRT. These eggs were randomly assigned to 2 different groups.

The first group of 76 fertile eggs was administered the vaccine in ovo on day 24 of incubation. The first day of incubation is considered day 0. Eggs are laid approximately 2-7 days before incubation. Poulvac® TRT (batch TR015, expiration date 24 June 1997 containing a titer of $10^{7.5}$ $TCID_{50}$) was used to prepare the in ovo vaccine. Three vials of the commercial product were each resuspended in 10 ml of sterile saline to give a resulting suspension having a titer of $10^{5.5}TCID_{50}$ of vaccine per 0.1 ml. These contents were well mixed and pooled. The mixed/pooled contents are redesignated as the "IOV" hereinafter in Example 1.

The in ovo administration used 0.1 ml of the IOV per egg containing a titer of $10^{5.5}TCID_{50}$, injected into the amniotic fluid of each of the 76 fertile eggs. Thereafter, these eggs were immediately placed into an incubator (without turning) and left to hatch in the isolation pen in which they were housed. These eggs/hatchlings are referred to as the vaccinated birds.

A second group of 66 fertile eggs were not vaccinated and were left to hatch under similar conditions in a second isolation pen. These eggs/hatchlings are referred to as the negative control birds.

For both the vaccinated birds and the negative control birds, hatching was recorded on days 27, 28, and 29 of incubation. Table 1 presents the experimentally-observed hatchability percentages. With respect to hatchability, the in ovo vaccination of the present invention produced excellent results with 93.4% of the vaccinated eggs hatching versus 92.4% of the negative control eggs hatching.

TABLE 1

Hatchability Percentages

| Birds | Day 27 | Day 28 | Day 29 | Total |
|---|---|---|---|---|
| Vaccinated | 19.7% | 73.7% | 0% | 93.4% |
| Negative Control | 28.8% | 63.6% | 0% | 92.4% |

After hatching, 25 poults from each group (i.e., the vaccinated birds and the negative control birds) were selected at random and placed on the floor on shavings in each of the respective isolation pens. The remaining birds from each group were culled.

Within each group, each bird was examined daily for clinical signs for a period of 21 days. The presence of nasal exudate was assessed by squeezing the beak. The severity of clinical disease was scored according to Table 2.

TABLE 2

Clinical Scoring System

| score | experimentally-observed symptoms |
|---|---|
| 0 | none |
| 1 | clear nasal exudate |
| 2 | turbid nasal exudate |
| 3 | swollen infraorbital sinuses or frothy eyes and 1 or 2 |

The total daily score of a group of birds was calculated by summarizing the individual scores of each bird on that day. Table 3 presents the experimentally-observed clinical signs using the relative scoring system of Table 2.

TABLE 3

Clinical Examination Results of Vaccinated Birds

| | Age in days of the examined bird | | | | | | | | |
|---|---|---|---|---|---|---|---|---|---|
| Bird # | 3 | 4 | 5 | 6 | 7 | 8 | 9 | 10 | 11 |
| 76 | 0 | 0 | 0 | 0 | 0 | 0 | 0 | 0 | 0 |
| 77 | 0 | 0 | 1 | 1 | 0 | 0 | 0 | 0 | 0 |
| 78 | 0 | 0 | 1 | 0 | 2 | 0 | 0 | 0 | 0 |
| 79 | 0 | 0 | 0 | 2 | 0 | 0 | 0 | 0 | 0 |
| 80 | 0 | 0 | 0 | 0 | 0 | 0 | 0 | 0 | 0 |
| 81 | 0 | 0 | 0 | 0 | 0 | 0 | 0 | 0 | 0 |
| 82 | 0 | 0 | 0 | 0 | 0 | 0 | 0 | 0 | 0 |
| 83 | 0 | 0 | 0 | 0 | 0 | 0 | 0 | 0 | 0 |
| 84 | 0 | 0 | 0 | 0 | 0 | 0 | 0 | 1 | 0 |
| 85 | 0 | 0 | 0 | 0 | 0 | 0 | 0 | 0 | 0 |
| 86 | 0 | 0 | 0 | 0 | 0 | 0 | 0 | 0 | 0 |
| 87 | 0 | 0 | 0 | 2 | 1 | 2 | 0 | 0 | 0 |
| 88 | 0 | 0 | 0 | 0 | 0 | 0 | 0 | 0 | 0 |
| 89 | 0 | 0 | 0 | 0 | 0 | 0 | 0 | 0 | 0 |
| 90 | 0 | 2 | 2 | 2 | 2 | 0 | 0 | 0 | 0 |
| 91 | 0 | 0 | 0 | 1 | 2 | 2 | 2 | 0 | 0 |
| 92 | 0 | 0 | 0 | 0 | 0 | 0 | 0 | 0 | 0 |
| 93 | 0 | 0 | 0 | 0 | 0 | 0 | 0 | 0 | 0 |
| 94 | 0 | 0 | 0 | 0 | 0 | 0 | 0 | 0 | 0 |
| 95 | 0 | 0 | 0 | 0 | 0 | 0 | 0 | 0 | 0 |
| 96 | 0 | 0 | 0 | 0 | 0 | 0 | 0 | 0 | 0 |
| 97 | 0 | 0 | 0 | 1 | 0 | 0 | 0 | 0 | 0 |
| 98 | 0 | 0 | 0 | 0 | 0 | 0 | 0 | 0 | 0 |
| 99 | 0 | 0 | 0 | 0 | 0 | 0 | 0 | 0 | 0 |
| 100 | 0 | 0 | 0 | 0 | 0 | 0 | 2 | 0 | 0 |
| Total | 0 | 2 | 4 | 9 | 7 | 4 | 4 | 1 | 0 |
| Mean Score/ Bird | 0 | 0.08 | 0.16 | 0.36 | 0.28 | 0.16 | 0.16 | 0.04 | 0 |
| # Positive | 0 | 1 | 3 | 6 | 4 | 2 | 2 | 1 | 0 |

The negative control birds were likewise examined for any clinical signs and, no abnormalities were observed, i.e., all had a score of zero.

The results of the above observations establish the safety of the in ovo vaccination methods of the present invention. The highest Mean Score/Bird (i.e., 0.36) for 6-day old birds provided an adequate margin of safety and indicated only slight/mild symptoms of TRT.

Serological analysis was also performed by collecting blood collected from 10 birds within the parent turkey flock 6½ weeks after the date that the eggs were received. Blood was also collected from the following 4 sets of birds: (a) at an age of 1 day, from 20 negative control birds; (b) at an age of 21 days, from 21 negative control birds; (c) at an age of 1 day, from 20 vaccinated birds; and (d) at an age of 21 days, from 20 vaccinated birds.

Serological analysis of the individual blood samples indicated titers of antibodies to TRTV. This analysis used an enzyme-linked immunosorbent assay (ELISA) technique which uses an A type antigen and expressed as ${}^2$log titers. Experimentally-measured titers of ${}^2$log titer≧6.0 were taken to be positive. The geometrical mean (GM) and standard deviation (SD) for the experimentally-measured titers were also calculated. The titer analysis established the following results. The parent turkey flock was free of TRTV [see GM=5.04 in comparison to the ≧6.0 positive cut-off value]. Of the 10 birds, one had an elevated titer of 7.7. Further, the GM titers for the 1-day old negative control birds and vaccinated birds were almost identical; i.e., respectively, 4.05 and 4.06. However, two birds among the vaccinated birds had positive titers [see titer values of 7.1 and 8.1—each ≧6.0]. By contrast, none of the negative control birds had titers≧6.0. The SD for the negative control birds and the vaccinated birds were, respectively, 0.82 and 1.46.

The 21-day old blood sampling tests also showed clear differences in the experimentally-measured titers. For the negative control birds, the GM decreased to 3.53 and the SD decreased to 0.46. In direct contrast, for the vaccinated birds, the GM increased to 10.53 and the SD increased to 0.85. Accordingly, the vaccinated birds had greatly elevated titers to TRTV.

In the vaccinated birds, the serological response at an age of 21 days was very high. This response was even higher than that typically encountered using the same dose (via eye drop vaccination) for 1-day old birds. TRTV antibody titers having a GM=10.5 are normally only seen following a challenge with a virulent strain of TRTV. For comparison, two trials using eye drop vaccinations with $10^{5.5}$TCID$_{50}$ Poulvac® TRT to susceptible turkey poults (at an age of 1 day) yielded mean antibody titers of, respectively, 8.3 and 8.7 for blood samples collected at an age of 21 days.

Table 4 presents the data supporting this serological testing of the parent turkey flock, the negative control birds, and the vaccinated birds.

TABLE 4

| | TRTV Titers | | | | |
|---|---|---|---|---|---|
| | Parent Flock | Negative Control Birds | | Vaccinated Birds | |
| | 6½ weeks | 1-day age | 21-day age | 1-day age | 21-day age |
| | 3.7 | 3.0 | 3.8 | 5.6 | 11.4 |
| | 5.5 | 3.0 | 3.7 | 3.9 | 10.4 |
| | 4.7 | 4.5 | 3.8 | 4.9 | 9.5 |
| | 5.9 | 4.3 | 3.0 | 3.4 | 11.6 |
| | 7.7 | 3.0 | 3.0 | 4.0 | 9.3 |
| | 5.6 | 4.8 | 3.4 | 3.0 | 9.9 |
| | 5.4 | 4.2 | 3.6 | 3.0 | 11.8 |
| | 3.7 | 4.7 | 3.6 | 3.0 | 11.1 |
| | 5.2 | 3.9 | 4.2 | 3.0 | 11.0 |
| | 3.0 | 3.0 | 4.5 | 7.1 | 9.7 |
| | | 4.7 | 4.3 | 5.2 | 11.1 |
| | | 5.0 | 3.2 | 3.9 | 9.1 |
| | | 3.0 | 3.9 | 4.4 | 11.3 |
| | | 4.8 | 3.0 | 3.0 | 10.6 |
| | | 3.3 | 3.8 | 8.1 | 11.5 |
| | | 5.1 | 3.5 | 3.3 | 11.2 |
| | | 4.5 | 3.0 | 3.0 | 10.5 |
| | | 4.1 | 3.0 | 3.0 | 10.0 |
| | | 5.1 | 3.5 | 3.0 | 9.9 |
| | | 3.0 | 3.3 | 3.5 | 9.6 |
| | | | 3.0 | | |
| GM | 5.04 | 4.05 | 3.53 | 4.06 | 10.53 |
| SD | 1.35 | 0.82 | 0.46 | 1.46 | 0.85 |

Thus, in ovo administration (at day 24 of incubation) of an IOV of the present invention at $10^{5.5}$ TCID$_{50}$ to fertile turkey eggs provides the necessary safety with respect to both hatchability and clinical signs, as well as an enhanced immune response over conventionally administered vaccines.

Example 2

Safety Study for in ovo Chicken Administration

Specific pathogen-free (hereinafter, "SPF) White Leghorn eggs were obtained from a commercial source (Broekman Instituut BV, Someren, The Netherlands). 126 SPF eggs were placed in an incubator, and after 18 days of incubation, the eggs were candled. This resulted in 5 non-fertilized eggs being rejected and 115 fertilized eggs being accepted. Of the 115 accepted eggs, 100 were randomly selected for in ovo vaccination. These 100 eggs were divided into three groups as follows:

Group 1 eggs/hatchlings were tagged for identification with an orange wing mark comprising a number. Group 1 consisted of 30 eggs which, as described below, received an in ovo vaccine at a per egg calculated dose of a titer of $10^{5.5}$ TCID$_{50}$.

Group 2 eggs/hatchlings were tagged for identification with a green wing mark comprising a number. Group 2 consisted of 40 eggs which, as described below, received an in ovo saline solution of equal volume to the vaccine injected to the Group 1 eggs.

Group 3 eggs/hatchlings were not tagged. Group 3 consisted of 30 eggs which did not receive any in ovo administration (either of the vaccine or of the saline solution).

The number on the wing marks was used only if the chick showed clinical signs of either TRT or SHS.

The chickens of both Groups 1 and 2 were housed in the same animal room in which they hatched. Appropriate conditions (e.g., feed, drinking water, wood shavings as bedding materials, temperatures, relative humidities, etc.) were maintained.

The time schedule for this experiment was as follows: The first day of incubation of the eggs of Groups 1, 2, and 3 was termed day 0 of incubation. The date of in ovo administration to the eggs of Group 1 and Group 2 of, respectively, a vaccine and a saline solution was day 18 of incubation. The calculated hatching date corresponded to day 21 of incubation. The study was concluded on a post-hatch date equivalent to day 46 of incubation.

To prepare the vaccine for in ovo administration, a commercially-available vaccine, Poulvac® TRT containing 2000 doses per vial, available from Fort Dodge Animal Health in Fort Dodge, Ia. or Weesp, The Netherlands was used. On a per dose basis, this vaccine had a titer of $10^{4.2}$ TCID$_{50}$. Twelve (12) vials of this vaccine were resuspended in phosphate-buffered-saline (hereinafter, "PBS"), using 5 ml of PBS per vial of vaccine. The resulting contents were well mixed and pooled. The resuspended material had a calculated titer of $10^{5.5}$ TCID$_{50}$ and a total volume of 60 ml. This vaccine is hereinafter referred to as the "IOV".

On day 18 of incubation, the IOV vaccine was administered in ovo via injection using a commercially-available Inovoject® egg injection machine from Embrex, Inc., North Carolina to the eggs of Group I. The egg-injection administration of the IOV was conducted in accordance with standard procedures. In like manner, a commercially-available saline solution, CLEAR-FLEX® INFUSIEVLOESISTOF, from Bieffle Medital SpA, Italy was administered to the eggs of Group 2.

Table 5 shows the treatment of the eggs within Groups 1, 2, and 3.

TABLE 5

| Treatment Of Eggs | | |
|---|---|---|
| Group # | # eggs/group | calculated dose per egg |
| 1 | 30 | $10^{5.5}$ $TCID_{50}$ vaccine |
| 2 | 40 | only saline solution |
| 3 | 30 | no treatment |

The hatchability percentages of eggs from Groups 1, 2, and 3 were experimentally observed and calculated. In brief, the following exceptions were noted. Because of spina bifida skeletal abnormalities (which were not attributed to any adverse action of the in ovo vaccination), two chicks from Group 1 were removed from the study directly after they were hatched and before they were tagged with an identifying wing mark. These two chicks were excluded from the Group 1 calculated hatchability percentages. Also from Group 1, one chick was injured on the toes and removed from the study after it had been tagged. Post-mortem examination of this chick revealed no signs of either TRT or of any other disease or of any other disorders. This one chick was likewise excluded from the Group 1 calculated hatchability percentages. With respect to the eggs/hatchlings of Group 2, one chick died after being hatched but before being tagged with an identifying wing mark. This chick was similarly excluded from the Group 2 calculated hatchability percentages.

As planned, the hatchlings of both Groups 1 and 2 were studied and examined for a 25-day observation period. During this period, none of the chicks showed clinical signs of either TRT or SHS. All 30 eggs of Group 3 hatched. On the day they hatched, all 30 chicks were decapitated for blood sampling and subsequent analysis as described later.

Table 6 presents the experimentally-observed hatchability and mortality results for each of Groups 1, 2, and 3. These results established that the in ovo vaccination of the present invention was safe with respect both hatchability and clinical signs of TRT and/or SHS.

TABLE 6

| Hatchability/Mortality Results | | | |
|---|---|---|---|
| | Group 1 (orange wing mark) vaccine | Group 2 (green wing mark) saline | Group 3 (no wing mark) no treatment |
| Incubated | 30 | 40 | 30 |
| Vaccinated | 30 | 40 | 0 |
| Hatched | 28 | 40 | 30 |
| | Percentage of eggs: | | |
| Vaccinated | 100 | 100 | 0 |
| Hatched | 93.3 | 100 | 100 |

The body weights of the chicks from both Group 1 (vaccine) and Group 2 (saline) were obtained on day 25. Mean body weight of the Group 1 chicks was 209 grams with a standard deviation of 22.1. For the Group 2 chicks, the mean body weight was 217 grams with a standard deviation of 24.8. The body weights of Groups 1 and 2 did not differ significantly as statistically determined using a 2-sided Student's t test with P=0.18). These results established that the in ovo vaccination of the present invention did not compromise the resulting day 25 body weight (which is commercially important) in comparison to that obtained with an in ovo injection of a physiological saline solution.

To confirm the TRT-free status of the SPF eggs used in Groups 1, 2, and 3, on the day the Group 3 eggs hatched, the chicks were killed by decapitation and blood samples were collected and analyzed. ELISA testing did not detect any antibodies to TRTV which confirms the TRT-free status of the SPF eggs used in this study.

This study established that the in ovo vaccination to SPF chicken eggs was safe with respect to each of hatchability, mortality, clinical signs of TRT and/or SHS, and day 25 body weight.

Example 3

Efficacy Study for in ovo SPF Chicken Vaccines

The aim of this study was to ascertain whether in ovo vaccination of 18-day old-chicken embryos is efficacious in preventing TRT and/or SHS disease after virulent challenge at 3 or 6 weeks of age. As established below, in ovo vaccination of susceptible 18-day-old fertile SPF chicken eggs with $10^{4.2}$ $TCID_{50}$ is safe while a dose of $10^{3.2}$ $TCID_{50}$ is efficacious against clinical disease.

Fertile eggs for hatching were obtained from a flock of SPF White Leghorn parents purchased from Whickham Laboratories, United Kingdom.

A commercially-available TRT vaccine, Poulvac® TRT, available from Fort Dodge Animal Health in Fort Dodge, Ia. or Weesp, The Netherlands was obtained. The in ovo vaccines of the present invention are prepared from this Poulvac® TRT as follows. Three (3) vials of the commercial vaccine containing a titer of $10^{7.5}$ $TCID_{50}$ were each resuspended in 4 ml of sterile water, and well mixed and pooled. Then 0.4 ml was removed and added to 19.6 ml of sterile PBS to give a final dilution equivalent to 200 ml per vial and a resulting suspension containing a titer of $10^{4.2}$ $TCID_{50}$ of vaccine per 0.1 ml. This vaccine was further diluted by removing 2 ml and adding it to 18 ml of sterile PBS to give a resulting suspension of $10^{3.2}$ $TCID_{50}$ of vaccine per 0.1 ml.

The challenge virus was prepared as follows. TRTV from the UK strain BUT 8544, isolated by Dr. R. C. Jones at Liverpool University (U.K.), was passaged 23 times in trachea organ culture (hereinafter, "TOC"), once in poults, reisolated, and passaged once more in TOC. The titer of this challenge virus was $10^{4.5}$ $TCID_{50}$ per ml.

After 18 days of incubation, a first set of 70 fertile eggs (hereinafter, "Set 1") were inoculated in ovo with 0.1 ml of the reconstituted TRT vaccine containing $10^{3.2}$ $TCID_{50}$ as described above. A second set of 70 eggs (hereinafter, "Set 2") was likewise inoculated with 0.1 ml of the reconstituted TRT vaccine containing $10^{4.2}$ $TCID_{50}$ as described above. The eggs were immediately placed into an incubator (without turning) and left to hatch in the pen in which they were housed. The eggs of Sets 1 and 2 were housed separately in similar isolation pens. A third set of 70 fertile eggs did not receive any in ovo administrations (hereinafter, "Set 3"). Set 3 is hereinafter referred to as the negative control birds. These eggs were housed in a third isolation pen.

Hatching was recorded on days 20, 21, 22, and 23 post incubation (day zero is first day of incubation). After hatch, excess birds were culled at one-day-old to leave fifty birds per set. For Sets 1, 2, and 3, the experimentally-recorded hatchability percentages were, respectively, 91%, 94%, and 92%. This establishes that, in ovo vaccination with titers of $10^{3.2}$ $TCID_{50}$ and $10^{4.2}$ $TCID_{50}$ were safe with respect to hatchability.

At three weeks of age, ten birds from each vaccinated group (i.e., Sets 1 and 2) and from the negative control birds (i.e., Set 3) were wing-tagged and moved into a fourth isolation pen. Each bird was then administered with the previously described challenge virus via an eye drop containing a dose of $10^{3.5}$ TCID$_{50}$ (virulent) TRTV in 0.1 ml. At 6 weeks of age, an additional 10 birds was likewise challenged with a virulent strain of TRTV. However, because of the increased age of these birds, the challenge dose was increased to $10^{3.8}$ TCID$_{50}$ (virulent) TRTV in 0.2 ml on a per bird basis.

The challenged birds were experimentally monitored for 14 days, after which they were bled and killed. The observed signs were recorded using the Table 2 Clinical Scoring System as used in Example 1. The total daily score of a group of birds was calculated by summarizing the individual scores of each bird on that day. The cumulative score is the sum of the mean daily scores at days 3-8. The $\chi 2$ test was used to analyze the data. The total clinical signs seen in the 2 vaccinated groups (Sets 1 and 2) from days 3-8 was compared to those seen in the (Set 3) positive controls on the same days for both the 3-week and 6-week challenges. This monitoring established the following results.

With respect to the 3-week challenge with the virulent TRTV strain at a titer of $10^{3.5}$ TCID$_{50}$, 90% of the unvaccinated control birds of Set 3 showed clinical signs. In direct contrast, smaller percentages of the vaccinated birds of Sets 1 and 2 showed clinical signs. For Set 1 (vaccinated with a titer of $10^{3.2}$ TCID$_{50}$ per egg), only 50% of the birds showed clinical signs. For Set 2 (vaccinated with a titer of $10^{4.2}$ TCID$_{50}$ per egg), only 30% of the birds showed clinical signs. In Set 3, only one bird remained completely clear of clinical signs. In contrast, five birds from Set 1 and seven birds from Set 2 remained completely clear of clinical signs.

With respect to the 6-week challenge with the virulent TRTV strain at a titer of $10^{3.8}$ TCID$_{50}$, 80% of the unvaccinated control birds of Set 3 showed clinical signs. In direct contrast, smaller percentages of the vaccinated birds of Sets 1 and 2 showed clinical signs. For Set 1 (vaccinated with a titer of $10^{3.2}$ TCID$_{50}$ per egg), only 20% of the birds showed clinical signs. For Set 2 (vaccinated with a titer of $10^{4.2}$ TCID$^{50}$ per egg), only 10% of the birds showed clinical signs.

$\chi 2$ statistical analysis established, for the 6-week challenge, that the experimentally-observed clinical signs in both vaccinated groups of birds (Sets 1 and 2) were significantly less severe than those recorded in the unvaccinated negative control birds of Set 3 (see P<0.01).

Tables 7, 8, and 9 present these results for, respectively, the 3-week challenge, the 6-week challenge, and the chi-squared statistical analysis as discussed above.

TABLE 7

Clinical Signs For 3-Week Challenge # of days post-challenge with virulent TRTV strain in eye drops at a dose of $10^{3.5}$ TCID$_{50}$ TRTV in 0.1 ml per bird

| bird # | 3 | 4 | 5 | 6 | 7 | 8 | 9 | 10 |
|---|---|---|---|---|---|---|---|---|
| for Set 1 (vaccinated with $10^{3.2}$ TCID$_{50}$) | | | | | | | | |
| 104 | 0 | 2 | 2 | 2 | 0 | 0 | 0 | 0 |
| 106 | 0 | 0 | 2 | 0 | 0 | 0 | 0 | 0 |
| 107 | 0 | 0 | 0 | 0 | 0 | 0 | 0 | 0 |
| 111 | 0 | 2 | 0 | 0 | 0 | 0 | 0 | 0 |
| 113 | 0 | 0 | 0 | 0 | 0 | 0 | 0 | 0 |

TABLE 7-continued

Clinical Signs For 3-Week Challenge # of days post-challenge with virulent TRTV strain in eye drops at a dose of $10^{3.5}$ TCID$_{50}$ TRTV in 0.1 ml per bird

| bird # | 3 | 4 | 5 | 6 | 7 | 8 | 9 | 10 |
|---|---|---|---|---|---|---|---|---|
| 117 | 0 | 0 | 0 | 0 | 0 | 0 | 0 | 0 |
| 118 | 0 | 1 | 2 | 2 | 0 | 0 | 0 | 0 |
| 124 | 0 | 0 | 0 | 0 | 0 | 0 | 0 | 0 |
| 127 | 0 | 0 | 0 | 0 | 0 | 0 | 0 | 0 |
| 139 | 0 | 0 | 1 | 2 | 0 | 0 | 0 | 0 |
| Total Daily Score | 0 | 5 | 7 | 6 | 0 | 0 | 0 | 0 |
| Mean Daily Score | 0 | 0.5 | 0.7 | 0.6 | 0 | 0 | 0 | 0 |
| Set 1 Cumulative Score per Bird = 1.8 for Set 2 (vaccinated with $10^{4.2}$ TCID$_{50}$) | | | | | | | | |
| 3 | 0 | 0 | 0 | 0 | 0 | 0 | 0 | 0 |
| 6 | 0 | 0 | 0 | 0 | 0 | 0 | 0 | 0 |
| 11 | 1 | 0 | 0 | 0 | 0 | 0 | 0 | 0 |
| 12 | 0 | 1 | 2 | 0 | 0 | 1 | 0 | 0 |
| 17 | 0 | 0 | 0 | 0 | 0 | 0 | 0 | 0 |
| 20 | 0 | 0 | 0 | 0 | 0 | 0 | 0 | 0 |
| 21 | 0 | 0 | 0 | 0 | 0 | 0 | 0 | 0 |
| 29 | 0 | 0 | 0 | 0 | 0 | 0 | 0 | 0 |
| 36 | 2 | 1 | 2 | 2 | 0 | 0 | 0 | 0 |
| 37 | 0 | 0 | 0 | 0 | 0 | 0 | 0 | 0 |
| Total Daily Score | 3 | 2 | 4 | 2 | 0 | 1 | 0 | 0 |
| Mean Daily Score | 0.3 | 0.2 | 0.4 | 0.2 | 0 | 0.1 | 0 | 0 |
| Set 2 Cumulative Score per Bird = 1.2 for Set 3 (not vaccinated) | | | | | | | | |
| 301 | 0 | 0 | 0 | 2 | 1 | 0 | 0 | 0 |
| 311 | 0 | 0 | 0 | 2 | 0 | 0 | 0 | 0 |
| 313 | 0 | 0 | 0 | 0 | 0 | 0 | 0 | 0 |
| 314 | 0 | 0 | 2 | 3 | 1 | 0 | 0 | 0 |
| 316 | 0 | 0 | 2 | 1 | 0 | 0 | 0 | 0 |
| 321 | 0 | 2 | 2 | 0 | 0 | 0 | 0 | 0 |
| 322 | 0 | 2 | 2 | 2 | 0 | 0 | 0 | 0 |
| 327 | 0 | 0 | 2 | 3 | 0 | 0 | 0 | 0 |
| 331 | 0 | 2 | 2 | 1 | 0 | 0 | 0 | 0 |
| 334 | 0 | 2 | 2 | 1 | 1 | 0 | 0 | 0 |
| Total Daily Score | 0 | 8 | 14 | 15 | 3 | 0 | 0 | 0 |
| Mean Daily Score | 0 | 0.8 | 1.4 | 1.5 | 0.3 | 0 | 0 | 0 |
| Set 3 Cumulative Score per Bird = 4.0 | | | | | | | | |

TABLE 8

Clinical Signs For 6-Week Challenge # of days post-challenge with virulent TRTV strain in eye drops at a dose of $10^{3.8}$ TCID$_{50}$ TRTV in 0.2 ml per bird

| bird # | 3 | 4 | 5 | 6 | 7 | 8 | 9 | 10 |
|---|---|---|---|---|---|---|---|---|
| for Set 1 (vaccinated with $10^{3.2}$ TCID$_{50}$) | | | | | | | | |
| 108 | 0 | 0 | 0 | 2 | 0 | 0 | 0 | 0 |
| 110 | 0 | 0 | 0 | 0 | 0 | 0 | 0 | 0 |
| 114 | 0 | 0 | 0 | 0 | 0 | 0 | 0 | 0 |
| 115 | 0 | 0 | 0 | 0 | 0 | 0 | 0 | 0 |
| 119 | 0 | 0 | 0 | 0 | 0 | 0 | 0 | 0 |
| 120 | 0 | 0 | 0 | 0 | 0 | 0 | 0 | 0 |
| 130 | 0 | 0 | 0 | 0 | 0 | 0 | 0 | 0 |
| 131 | 0 | 0 | 2 | 0 | 0 | 0 | 0 | 0 |

TABLE 8-continued

| Clinical Signs For 6-Week Challenge | | | | | | | | |
|---|---|---|---|---|---|---|---|---|
| | # of days post-challenge with virulent TRTV strain in eye drops at a dose of $10^{3.8}$ $TCID_{50}$ TRTV in 0.2 ml per bird | | | | | | | |
| bird # | 3 | 4 | 5 | 6 | 7 | 8 | 9 | 10 |
| 134 | 0 | 0 | 0 | 0 | 0 | 0 | 0 | 0 |
| 135 | 0 | 0 | 0 | 0 | 0 | 0 | 0 | 0 |
| Total Daily Score | 0 | 0 | 2 | 2 | 0 | 0 | 0 | 0 |
| Mean Daily Score | 0 | 0 | 0.2 | 0.2 | 0 | 0 | 0 | 0 |
| | Set 1 Cumulative Score per Bird = 0.4 | | | | | | | |
| | for Set 2 (vaccinated with $10^{4.2}$ $TCID_{50}$) | | | | | | | |
| 2 | 0 | 0 | 0 | 0 | 0 | 0 | 0 | 0 |
| 4 | 0 | 0 | 0 | 0 | 0 | 0 | 0 | 0 |
| 8 | 0 | 0 | 0 | 0 | 0 | 0 | 0 | 0 |
| 13 | 0 | 0 | 0 | 0 | 0 | 0 | 0 | 0 |
| 18 | 0 | 0 | 2 | 2 | 0 | 0 | 0 | 0 |
| 25 | 0 | 0 | 0 | 0 | 0 | 0 | 0 | 0 |
| 27 | 0 | 0 | 0 | 0 | 0 | 0 | 0 | 0 |
| 32 | 0 | 0 | 0 | 0 | 0 | 0 | 0 | 0 |
| 38 | 0 | 0 | 0 | 0 | 0 | 0 | 0 | 0 |
| 39 | 0 | 0 | 0 | 0 | 0 | 0 | 0 | 0 |
| Total Daily Score | 0 | 0 | 2 | 2 | 0 | 0 | 0 | 0 |
| Mean Daily Score | 0 | 0 | 0.2 | 0.2 | 0 | 0 | 0 | 0 |
| | Set 2 Cumulative Score per Bird = 0.4 | | | | | | | |
| | for Set 3 (not vaccinated) | | | | | | | |
| 302 | 0 | 1 | 0 | 0 | 0 | 0 | 0 | 0 |
| 306 | 0 | 0 | 0 | 3 | 0 | 0 | 0 | 0 |
| 307 | 0 | 0 | 0 | 0 | 0 | 0 | 0 | 0 |
| 312 | 0 | 0 | 0 | 0 | 2 | 0 | 0 | 0 |
| 315 | 0 | 0 | 0 | 0 | 0 | 0 | 0 | 0 |
| 318 | 0 | 0 | 3 | 3 | 0 | 0 | 0 | 0 |
| 319 | 0 | 0 | 1 | 2 | 2 | 2 | 0 | 0 |
| 329 | 0 | 0 | 1 | 0 | 0 | 0 | 0 | 0 |
| 330 | 0 | 2 | 2 | 2 | 2 | 0 | 0 | 0 |
| 332 | 0 | 0 | 0 | 0 | 2 | 0 | 0 | 0 |
| Total Daily Score | 0 | 3 | 7 | 10 | 8 | 2 | 0 | 0 |
| Mean Daily Score | 0 | 0.3 | 0.7 | 1.0 | 0.8 | 0.2 | 0 | 0 |
| | Set 3 Cumulative Score per Bird = 3.0 | | | | | | | |

TABLE 9

Chi-Squared Analysis
$\chi 2$ - Analysis of Clinical Scores: Comparison of 2 Vaccinated Groups (Sets 1 and 2) with 1 Negative Control Group (Set 3)

| Group | $\chi 2$ | Deg. of Freedom | Probability |
|---|---|---|---|
| Set 1 (3-week challenge) | 7.27 | 3 | 0.1 > P > 0.05 |
| Set 2 (3-week challenge) | 10.133 | 3 | 0.02 > P > 0.05 |
| Set 1 (6-week challenge) | 12.09 | 3 | P < 0.01 |
| Set 2 (6-week challenge) | 12.09 | 3 | P < 0.01 |

In addition to monitoring the birds of Sets 1, 2, and 3 for clinical signs of TRT, the birds were also subjected to serological analysis wherein antibodies to TRTV in individual blood samples were determined by ELISA techniques using an A type antigen and expressed as $^2$log titers. Antibody titers of $^2$log titer>6.0 were taken to be positive. The results were statistically analyzed using a Student's t-test for unpaired data. Tables 10 and 11 present the serological results obtained with the challenged birds of Sets 1, 2, and 3 for, respectively, the 3-week challenge and the 6-week challenge. In Tables 10 and 11, "PC" refers to post-challenge; "GM" refers to geometric mean; and "SD" refers to standard deviation. In brief, all the groups (i.e., Sets 1, 2, and 3) showed a significant rise in antibody titers at 7 post-challenge days and a additional rise in antibody titers at 14 days PC.

TABLE 10

| TRTV Antibody Titers (3-Week Challenge) | | | |
|---|---|---|---|
| | $^2$log antibody titers after challenge with virulent TRTV in eye drops at a dose of $10^{3.5}$ $TCID_{50}$ in 0.1 ml per bird | | |
| bird # | prior to challenge | 7 days PC | 14 days PC |
| | for Set 1 (vaccinated with $10^{3.2}$ $TCID_{50}$) | | |
| 104 | 4.4 | | 9.9 |
| 106 | 3.6 | 9 | 9.9 |
| 107 | 6.2 | 7 | 9.5 |
| 111 | 6.6 | 10.4 | 11.2 |
| 113 | 3.4 | | 9.4 |
| 117 | 3.5 | | 8.8 |
| 118 | 3.6 | 6.4 | 9.5 |
| 124 | 3.2 | 6.8 | 9.7 |
| 127 | 10.1 | | 10.9 |
| 139 | 3.4 | | 10.2 |
| GM | 4.8 | 7.92 | 9.9 |
| SD | 2.22 | 1.71 | 0.72 |
| | for Set 2 (vaccinated with $10^{4.2}$ $TCID_{50}$) | | |
| 3 | 4.4 | 9 | 9.9 |
| 6 | 9.7 | | 10.6 |
| 11 | 4.6 | 10.3 | 10.9 |
| 12 | 4.3 | 7.5 | 10 |
| 17 | 8.4 | 10.6 | 11.1 |
| 20 | 9.1 | | |
| 21 | 4.5 | | 10 |
| 29 | 4.4 | | 10 |
| 36 | 3.6 | 9.6 | 10 |
| 37 | 4.8 | | 10.1 |
| GM | 5.78 | 9.4 | 10.29 |
| SD | 2.31 | 1.23 | 0.45 |
| | for Set 3 (not vaccinated) | | |
| 301 | 3.3 | | 9.2 |
| 311 | 3.4 | 9.1 | 9.9 |
| 313 | 3 | 9 | 9.7 |
| 314 | 3.7 | 9.9 | 10.3 |
| 316 | 3.7 | | 10.2 |
| 321 | 4.2 | 9.5 | 9.8 |
| 322 | 3.9 | 7.7 | 10 |
| 327 | 3.4 | | 10 |
| 331 | 3.5 | | 10.5 |
| 334 | 3.5 | | 10.3 |
| GM | 3.56 | 9.04 | 9.99 |
| SD | 0.28 | 0.83 | 0.37 |

TABLE 11

| TRTV Antibody Titers (6-Week Challenge) | | | |
|---|---|---|---|
| | $^2$log antibody titers after challenge with virulent TRTV in eye drops at a dose of $10^{3.8}$ $TCID_{50}$ in 0.2 ml per bird | | |
| bird # | prior to challenge | 7 days PC | 14 days PC |
| | for Set 1 (vaccinated with $10^{3.2}$ $TCID_{50}$) | | |
| 108 | 4 | | 10.2 |
| 110 | 5.9 | | 10.1 |
| 114 | 4.7 | | 9.8 |

TABLE 11-continued

TRTV Antibody Titers (6-Week Challenge)

| bird # | $^2$log antibody titers after challenge with virulent TRTV in eye drops at a dose of $10^{3.8}$ $TCID_{50}$ in 0.2 ml per bird prior to challenge | 7 days PC | 14 days PC |
|---|---|---|---|
| 115 | 4 | 6 | 9.9 |
| 119 | 4.1 | 6.5 | 10.7 |
| 120 | 4 | | 10.4 |
| 130 | 3.9 | | 9.8 |
| 131 | 3.5 | 7 | 9.9 |
| 134 | 3.9 | 6.4 | 9.6 |
| 135 | 4 | 5.5 | 10 |
| GM | 4.2 | 6.28 | 10.04 |
| SD | 0.67 | 0.56 | 0.32 |
| | for Set 2 (vaccinated with $10^{4.2}$ $TCID_{50}$) | | |
| 2 | 5.8 | | 10 |
| 4 | 7.1 | | 9.3 |
| 8 | 6.4 | 10.3 | 10.4 |
| 13 | 5.2 | | 10.2 |
| 18 | 8.6 | 10.2 | 11.2 |
| 25 | 10.4 | 10.7 | 10.9 |
| 27 | 10.2 | 10.5 | 11.4 |
| 32 | 10.3 | | |
| 38 | 10.8 | 10.9 | 11.1 |
| 39 | 6.8 | | 9.5 |
| GM | 8.16 | 10.52 | 10.47 |
| SD | 2.14 | 0.29 | 0.72 |
| | for Set 3 (not vaccinated) | | |
| 302 | 3.8 | 7.1 | 10.4 |
| 306 | 4.4 | 8.1 | 10.1 |
| 307 | 4.1 | | 10.1 |
| 312 | 3.8 | 6.3 | 9.9 |
| 315 | 4.1 | 6 | 9.9 |
| 318 | 3.9 | | 10 |
| 319 | 4.2 | | 9.9 |
| 329 | 3.8 | | 9.9 |
| 330 | 4.3 | 7.7 | 9.7 |
| 332 | 3.4 | | 9.9 |
| GM | 3.98 | 7.04 | 9.98 |
| SD | 0.30 | 0.89 | 0.19 |

A similar serological analysis was also performed with respect to all three groups (i e., Sets 1, 2, and 3) which were not challenged with a virulent strain of TRTV. Mean antibody titers from the control birds (Set 3) and from the 2 groups of vaccinated birds (Sets 1 and 2) from one-day old to 8½-weeks old were determined. As expected, the antibody titers for the control birds remained low throughout this study. The titers of the control birds were statistically compared to those of the vaccinated birds of the same age. Table 12 presents the post in ovo determined mean antibody titers. Individual results were available (data not shown) to support the experimental results presented in Table 12. In Table 12, "n" refers to the number of birds and "SD" refers to the Standard Deviation.

TABLE 12

Post In Ovo Mean Antibody Titers

| Age | n | SD | Mean Antibody Titer |
|---|---|---|---|
| | for Set 1 (vaccinated with $10^{3.2}$ $TCID_{50}$) | | |
| 1-Day Old | 10 | 0.87 | 4.95 |
| 1 Week | 5 | 0.51 | 4.06 |
| 2 Weeks | 5 | 1.54 | 3.88 |
| 3 Weeks | 20 | 1.71 | 4.06 |
| 4 Weeks | 5 | 0.22 | 4.28 |
| 5 Weeks | 10 | 0.67 | 4.55 |
| 6 Weeks | 10 | 0.67 | 4.2 |
| 8½ Weeks | 10 | 2.04 | 5.83 |
| | for Set 2 (vaccinated with $10^{4.2}$ $TCID_{50}$) | | |
| 1-Day Old | 11 | 0.56 | 4.3 |
| 1 Week | 5 | 0.45 | 4.26 |
| 2 Weeks | 5 | 2.82 | 4.76 |
| 3 Weeks | 20 | 2.42 | 5.98 |
| 4 Weeks | 5 | 2.98 | 7.16 |
| 5 Weeks | 10 | 2.38 | 7.03 |
| 6 Weeks | 10 | 2.12 | 8.14 |
| 8½ Weeks | 9 | 2.56 | 8.13 |
| | for Set 3 (not vaccinated) | | |
| 1-Day Old | 10 | 0.73 | 3.88 |
| 1 Week | 5 | 0.96 | 4.72 |
| 2 Weeks | 5 | 0.26 | 3.8 |
| 3 Weeks | 18 | 0.27 | 3.49 |
| 4 Weeks | 5 | 0.17 | 4.4 |
| 5 Weeks | 11 | 0.55 | 3.61 |
| 6 Weeks | 11 | 0.35 | 3.92 |
| 8½ Weeks | 9 | 0.86 | 3.98 |

An analysis of the results of Example 3, including the experimentally-obtained measurements, results, and corresponding statistical analysis, indicates that the lower dose of vaccine ($10^{3.2}$ $TCID_{50}$ TRTV delivered in ovo to susceptible 18-day-old fertile SPF chicken eggs) was efficacious in that it conferred significant protection against challenge with a virulent strain of TRTV at 6 weeks of age. At 3 weeks of age, protection was also observed; however, in light of the number of birds, the experimentally-observed differences in the protection afforded fell just beneath the level of significance. At the increased vaccination dose of $10^{4.2}$ $TCID_{50}$ TRTV per egg (an increase on the order of approximately $^1$log10), for both the 3-week and the 6-week challenges, significant protection against exposure to a virulent strain of TRTV was observed.

In ovo administration of the vaccine derived from the Poulvac® TRT was clearly associated with the production of TRTV-specific antibodies in the vaccinated/inoculated birds. This association appeared to be dose-dependent. The higher dose of the in ovo vaccine caused an increase in mean antibody titer at three weeks of age to levels significantly higher than those of the negative control birds and to levels closely below the cutoff value of 6.0. The circulating antibody response to the in ovo vaccination with the higher dose of $10^{4.2}$ $TCID_{50}$ per egg appeared to increase with the passage of time; a maximum was obtained at six weeks of age; and, thereafter, the titers remained steady until 8½ weeks of age.

In contrast to the above discussed results for the high vaccination dose, the birds given the lower dose of $10^{3.2}$ $TCID_{50}$ per egg appeared to experience a delayed antibody response to vaccination. Titers only started increasing at 8½ weeks of age—when they reached levels significantly higher than those of the control birds. At this time (i.e., 8½ weeks) the titers for the low vaccine birds (Set 1) were at similar levels to those of the high vaccine birds (Set 2) at an age of 3 weeks. It appeared likely that, with the passage of yet additional time beyond 8½ weeks, the antibody titers would have increased to levels above 6.0.

A relationship appeared between antibody titers and reduction in clinical signs of TRT. In each grouping of birds where the antibody titers were significantly higher than those of the control birds but nonetheless below the positive cutoff value of 6.0;—the observed reduction in clinical signs of TRT was statistically significant.

In ovo vaccination to susceptible day-18-old fertile SPF chicken eggs with doses in the approximate range of from at least $10^{3.2}$ $TCID_{50}$ per egg to at least $10^{4.2}$ $TCID_{50}$ per egg, and, in particular, with doses of approximately $10^{4.2}$ $TCID_{50}$ per egg appeared both safe and efficacious against clinical disease normally expected from challenge with a virulent strain of TRTV.

Example 4

Efficacy Study for in ovo Commercial Chicken Vaccines

The aim of this study was to ascertain whether in ovo vaccination of 18-day-old incubated fertile chicken eggs from a parent flock of commercial broilers is efficacious in preventing TRT and/or SHS disease after virulent challenge at 4 or 6 weeks of age. As established below, in ovo vaccination of susceptible 18-day-old fertile eggs from TRTV-antibody positive parents with $10^{3.2}$ $TCID_{50}$ per egg with a vaccine derived from Poulvac® TRT is efficacious against clinical rhinotracheitis disease.

Fertile eggs for hatching were obtained from a flock of 37-week-old commercial broiler parents which had been previously vaccinated with live TRT vaccine at 10 weeks of age and with killed TRT vaccine at 18 weeks of age. These eggs were obtained from the Mossbank breeder flock, Marshall Agriculture, Whitburn, Scotland.

A commercially-available TRT vaccine, Poulvac® TRT, available from Fort Dodge Animal Health, Fort Dodge, Ia. or Weesp, The Netherlands was used to prepare the in ovo vaccines of the present invention. Three vials of this commercial vaccine containing a titer of $10^{7.5}$ TCID50 were each resuspended in 5 ml of sterile water, and the contents well mixed and pooled. The vaccine was further diluted in sterile phosphate-buffered saline (PBS) to give a resulting suspension of $10^{3.2}$ $TCID_{50}$ of vaccine per 0.1 ml.

The challenge virus was prepared as follows. TRTV from the UK strain BUT 8544 (see page 12) was passaged 23 times in trachea organ culture (hereinafter, "TOC"), once in poults, reisolated, and passaged once more in TOC. The titer of this challenge virus was $10^{4.5}$ $TCID_{50}$ per ml.

After 18 days of incubation, 57 fertile eggs were inoculated in ovo with 0.1 ml of the reconstituted TRT vaccine containing $10^{3.2}$ $TCID_{50}$ as described above. The eggs were immediately placed into an incubator (without turning) and left to hatch in the isolation pen in which they were housed. After hatching, 40 birds were removed from the incubator and placed on the floor on shavings.

A number (110) of fertile eggs were not vaccinated/inoculated and were left to hatch separately. A day after hatching, forty birds were housed in a second isolation pen as the negative control birds. Challenged control birds were called positive control birds.

Hatching was recorded on days 20, 21, 22, and 23 (inoculation day—zero). After hatch, excess birds were humanely killed or used for the collection of blood. The hatchability percentages for the non-vaccinated eggs and the vaccinated eggs were, respectively, 89% and 91% which establishes that, with respect to hatchability, vaccination with a titer of $10^{3.2}$ $TCID_{50}$ was safe.

At 4 weeks of age, ten birds from the vaccinated group and ten birds from the negative controls were wing-tagged and moved into a third isolation pen. Each bird was then administered with the previously described challenge virus via an eye drop containing a dose of $10^{3.5}$ $TCID_{50}$ (virulent) TRTV in 0.1 ml. At 6 weeks of age, an additional 14 birds was likewise challenged with a virulent strain of TRTV. However, because of the increased age of these birds, the challenge dose was increased to $10^{3.8}$ $TCID_{50}$ (virulent) TRTV in 0.2 ml, on a per bird basis.

The challenged birds were experimentally monitored for 14 days after which they were bled and killed. The observed signs were recorded using Table 13 Revised Clinical Scoring System. The Table 13 system was similar to but not identical with the Table 2 system previously described in Example 1 above.

TABLE 13

Revised Clinical Scoring System

| Score | experimentally-observed symptoms |
|---|---|
| 0 | no signs |
| 1 | clear nasal exudate |
| 1 | frothy eyes but no nasal exudate (F) |
| 2 | turbid nasal exudate |
| 3 | swollen infraorbital sinuses or frothy eyes and 1 or 2 |

The total daily score of a group of birds was calculated by summarizing the individual scores of each bird on that day. The cumulative score is the sum of the mean daily scores. The $\chi 2$ test was used to analyze the data. The total clinical signs seen in the Set 1 vaccinated group was compared to those seen in the Set 2 positive controls on the same days for both the 4-week and 6-week challenges. This monitoring established the following results.

With respect to the 4-week challenge with the virulent TRTV strain at a titer of $10^{3.5}$ $TCID_{50}$, clinical signs were only observed on days 6 and 7,—the maximum signs were seen on day 6 in both groups (i.e., Sets 1 and 2). In the vaccinated group (Set 1), only 30% of the birds exhibited clinical signs after challenge and the cumulative mean score per bird was 0.6. In Set 1, seven out of ten birds remained completely clear of clinical signs. The total clinical signs seen in the vaccinated birds were statistically compared to those of the positive control birds. Although the vaccinated birds exhibited less severe clinical signs than those of the positive control birds, these results were not statistically significant ($0.2<P<0.3$).

With respect to the 6-week challenge with the virulent TRTV strain at a titer of $10^{3.8}$ $TCID_{50}$, clinical signs were observed for longer periods of time in the positive control birds than after the 4-week challenge with the lower dose. However, in the vaccinated birds, clinical signs were observed for only one day. Of the positive control birds, 57% showed clinical signs and the cumulative score per bird was 1.35. Of the 14 birds in this group, 6 remained completely clear of clinical signs. One bird showed severe clinical signs on days 5 and 6 of the observation period and subsequently died nine days after challenge. Post-mortem examination of this bird revealed a dilated right ventricle, congested cardiac veins, lung congestion, excess mucous in the trachea, and a fibrinous exudate on the liver. The probable cause of death was right heart failure and possible hepatitis. By contrast, only 14% of the vaccinated group of birds exhibited clinical signs after challenge and the cumulative score per bird was 0.14. Of the 14 birds in this group, 12 remained completely clear of clinical signs. The total clinical signs in the vaccinated group (Set 1) were statistically compared using a $\chi 2$ analysis to those seen in the positive control birds (Set 2). This analysis established that the clinical signs seen in the vaccinated group were significantly less severe than those seen in the positive control birds (0.02<P<0.05).

Tables 14, 15, and 16 present these results for, respectively, the 4-week challenge, the 6-week challenge, and the $x^2$ statistical analysis as discussed above.

TABLE 14

Clinical Signs For 4-Week Challenge

| bird # | # of days post-challenge with virulent TRTV strain in eye drops at a dose of $10^{3.5}$ TRTV $TCID_{50}$ in 0.1 ml per bird: 3 | 4 | 5 | 6 | 7 | 8 | 9 | 10 |
|---|---|---|---|---|---|---|---|---|
| | for Set 1 (vaccinated with $10^{3.2}$ $TCID_{50}$) | | | | | | | |
| 41 | 0 | 0 | 0 | 0 | F | 0 | 0 | 0 |
| 42 | 0 | 0 | 0 | 0 | 0 | 0 | 0 | 0 |
| 43 | 0 | 0 | 0 | 2 | 0 | 0 | 0 | 0 |
| 44 | 0 | 0 | 0 | 0 | 0 | 0 | 0 | 0 |
| 45 | 0 | 0 | 0 | 0 | 0 | 0 | 0 | 0 |
| 46 | 0 | 0 | 0 | 0 | 0 | 0 | 0 | 0 |
| 47 | 0 | 0 | 0 | 0 | 0 | 0 | 0 | 0 |
| 48 | 0 | 0 | 0 | 2 | F | 0 | 0 | 0 |
| 49 | 0 | 0 | 0 | 0 | 0 | 0 | 0 | 0 |
| 50 | 0 | 0 | 0 | 0 | 0 | 0 | 0 | 0 |
| Total Daily Score | 0 | 0 | 0 | 4 | 2 | 0 | 0 | 0 |
| Mean Daily Score | 0 | 0 | 0 | 0.4 | 0.2 | 0 | 0 | 0 |
| | Set 1 Cumulative Score per Bird = 0.6 | | | | | | | |
| | for Set 2 (nonvaccinated) | | | | | | | |
| 391 | 0 | 0 | 0 | 3 | 0 | 0 | 0 | 0 |
| 392 | 0 | 0 | 0 | 0 | 0 | 0 | 0 | 0 |
| 393 | 0 | 0 | 0 | 0 | 0 | 0 | 0 | 0 |
| 394 | 0 | 0 | 0 | 2 | 0 | 0 | 0 | 0 |
| 395 | 0 | 0 | 0 | 3 | F | 0 | 0 | 0 |
| 396 | 0 | 0 | 0 | 0 | F | 0 | 0 | 0 |
| 397 | 0 | 0 | 0 | 0 | 0 | 0 | 0 | 0 |
| 398 | 0 | 0 | 0 | 1 | F | 0 | 0 | 0 |
| 399 | 0 | 0 | 0 | 1 | 0 | 0 | 0 | 0 |
| 400 | 0 | 0 | 0 | 0 | 0 | 0 | 0 | 0 |
| Total Daily Score | 0 | 0 | 0 | 10 | 3 | 0 | 0 | 0 |
| Mean Daily Score | 0 | 0 | 0 | 1 | 0.3 | 0 | 0 | 0 |
| | Set 2 Cumulative Score per Bird = 1.3 | | | | | | | |

TABLE 15

Clinical Signs For 6-Week Challenge

| bird # | # of days post-challenge with virulent TRTV strain in eye drops at a dose of $10^{3.8}$ TRTV $TCID_{50}$ in 0.2 ml per bird: 3 | 4 | 5 | 6 | 7 | 8 | 9 | 10 |
|---|---|---|---|---|---|---|---|---|
| | for Set 1 (vaccinated with $10^{3.2}$ $TCID_{50}$) | | | | | | | |
| 1 | 0 | 0 | 0 | 0 | 0 | 0 | 0 | 0 |
| 2 | 0 | 0 | 0 | 0 | 0 | 0 | 0 | 0 |
| 3 | 0 | 0 | 0 | 0 | 0 | 0 | 0 | 0 |
| 52 | 0 | 0 | 0 | 0 | 0 | 0 | 0 | 0 |
| 53 | 0 | 0 | 0 | 0 | 0 | 0 | 0 | 0 |
| 54 | 0 | 0 | 0 | 0 | 0 | 0 | 0 | 0 |

TABLE 15-continued

Clinical Signs For 6-Week Challenge

| bird # | # of days post-challenge with virulent TRTV strain in eye drops at a dose of $10^{3.8}$ TRTV $TCID_{50}$ in 0.2 ml per bird: 3 | 4 | 5 | 6 | 7 | 8 | 9 | 10 |
|---|---|---|---|---|---|---|---|---|
| 55 | 0 | 0 | 0 | 0 | 0 | 0 | 0 | 0 |
| 56 | 0 | 0 | 0 | 0 | 0 | 0 | 0 | 0 |
| 57 | 0 | 0 | 0 | 0 | 0 | 0 | 0 | 0 |
| 59 | 0 | 0 | 0 | F | 0 | 0 | 0 | 0 |
| 60 | 0 | 0 | 0 | 0 | 0 | 0 | 0 | 0 |
| 62 | 0 | 0 | 0 | F | 0 | 0 | 0 | 0 |
| 65 | 0 | 0 | 0 | 0 | 0 | 0 | 0 | 0 |
| 69 | 0 | 0 | 0 | 0 | 0 | 0 | 0 | 0 |
| Total Daily Score | 0 | 0 | 0 | 2 | 0 | 0 | 0 | 0 |
| Mean Daily Score | 0 | 0 | 0 | 0.14 | 0 | 0 | 0 | 0 |
| | Set 1 Cumulative Score per Bird = 0.14 | | | | | | | |
| | for Set 2 (nonvaccinated) | | | | | | | |
| 381 | 0 | 0 | 0 | 0 | 0 | 0 | 0 | 0 |
| 383 | 0 | 0 | 0 | 0 | 0 | 0 | 0 | 0 |
| 387 | 0 | 0 | 0 | 0 | 0 | 0 | 0 | 0 |
| 388 | 0 | F | 0 | 0 | 0 | 0 | 0 | 0 |
| 389 | 0 | 0 | 0 | 0 | 0 | 1 | 0 | 0 |
| 390 | 0 | 0 | F | 0 | 0 | 0 | 0 | 0 |
| 463 | 0 | 0 | 2 | F | 0 | 1 | 0 | 0 |
| 464 | 0 | 0 | 0 | 0 | 0 | 0 | 0 | 0 |
| 465 | 0 | 0 | 0 | 2 | 0 | 0 | 0 | 0 |
| 469 | 0 | 0 | 0 | 0 | 0 | 1 | 0 | 0 |
| 474 | 0 | 0 | 0 | 0 | 0 | 0 | 0 | 0 |
| 476 | 0 | 0 | 3 | 3 | 0 | 0 | dead | 0 |
| 477 | 0 | 0 | 0 | 0 | 0 | 0 | 0 | 0 |
| 478 | 0 | 0 | 2 | F | 0 | 0 | 0 | 0 |
| Total Daily Score | 0 | 1 | 8 | 7 | 0 | 3 | 0 | 0 |
| Mean Daily Score | 0 | 0.07 | 0.57 | 0.5 | 0 | 0.21 | 0 | 0 |
| | Set 2 Cumulative Score per Bird = 1.35 | | | | | | | |

TABLE 16

Chi-Squared Analysis Of Clinical Score Data
$\chi 2$ - Analysis of Clinical Scores: Comparison of 1 Vaccinated Group (Set 1) with 1 Positive Control Group (Set 2)

| Group | $\chi 2$ | Deg. of Freedom | Probability |
|---|---|---|---|
| Set 1 (4-week challenge) | 3.95 | 3 | 0.2 < P < 0.3 |
| Set 1 (6-week challenge) | 8.43 | 3 | 0.02 < P < 0.05 |

In addition to monitoring the birds of Sets 1 and 2 for clinical signs of TRT, the birds were also subjected to serological analysis wherein antibodies to TRTV in individual blood samples were determined by ELISA techniques developed at Leahurst, Liverpool, (U.K.) using an A type antigen and expressed as $^2$log titers. Antibody titers of $^2$log titer>6.0 were taken to be positive. The results were statistically analyzed using a Student's t-test for unpaired data. Tables 17 and 18 present the serological results obtained with the challenged birds of Sets 1 and 2 for, respectively, the 4-week challenge and the 6-week challenge. In Tables 17 and 18, "PC" refers to post-challenge.

TABLE 17

TRTV Antibody Titers (4-Week Challenge)

| bird # | $^2$log antibody titers after challenge with virulent TRTV in eye drops at a dose of $10^{3.5}$ $TCID_{50}$ in 0.1 ml per bird: prior to challenge | 14 days PC |
|---|---|---|
| | for Set 1 (vaccinated with $10^{3.2}$ $TCID_{50}$) | |
| 41 | 3.0 | 9.4 |
| 42 | 3.0 | 9.2 |
| 43 | 3.0 | 10.1 |
| 44 | 3.0 | 9.5 |
| 45 | 6.9 | 10.8 |
| 46 | 5.4 | 11.2 |
| 47 | 3.0 | 10.2 |
| 48 | 3.0 | 10.6 |
| 49 | 8.2 | 9.9 |
| 50 | 9.2 | 11.0 |
| Mean | 4.77 | 10.19 |
| Standard Deviation | 2.48 | 0.70 |
| | for Set 2 (nonvaccinated) | |
| 391 | 3.3 | 9.5 |
| 392 | 3.5 | 10.3 |
| 393 | 3.0 | 9.7 |
| 394 | 3.1 | 9.1 |
| 395 | 3.6 | 8.9 |
| 396 | 3.6 | 9.7 |
| 397 | 3.1 | 9.8 |
| 398 | 3.4 | 9.3 |
| 399 | 3.0 | 9.7 |
| 400 | 3.4 | 9.9 |
| Mean | 3.3 | 9.6 |
| Standard Deviation | 0.24 | 0.41 |

TABLE 18

TRTV Antibody Titers (6-Week Challenge)

| bird # | $^2$log antibody titers after challenge with virulent TRTV in eye drops at a dose of $10^{3.8}$ $TCID_{50}$ in 0.2 ml per bird: prior to challenge | 14 days PC |
|---|---|---|
| | for Set 1 (vaccinated with $10^{3.2}$ $TCID_{50}$) | |
| 1 | 6.3 | 11.6 |
| 2 | 4.3 | 10.4 |
| 3 | 4.2 | 10.1 |
| 52 | 3.6 | 10.6 |
| 53 | 4.1 | 10.6 |
| 54 | 3.7 | 10.7 |
| 55 | 4.8 | 9.7 |
| 56 | 3.6 | 9.9 |
| 57 | 8.1 | 10.1 |
| 59 | 3.4 | 10.2 |
| 60 | 3.6 | 9.8 |
| 62 | | 9.3 |
| 65 | 5.3 | 10.0 |
| 69 | 4.9 | 10.1 |
| Mean | 4.61 | 10.22 |
| Standard Deviation | 1.34 | 0.55 |
| | for Set 2 (nonvaccinated) | |
| 381 | 4.2 | 9.8 |
| 383 | 5.2 | 9.2 |
| 387 | 3.0 | 9.9 |
| 388 | 3.4 | 9.6 |
| 389 | 3.8 | 9.0 |
| 390 | 5.4 | 8.8 |
| 463 | 4.0 | 10.0 |

TABLE 18-continued

TRTV Antibody Titers (6-Week Challenge)

| bird # | $^2$log antibody titers after challenge with virulent TRTV in eye drops at a dose of $10^{3.8}$ $TCID_{50}$ in 0.2 ml per bird: prior to challenge | 14 days PC |
|---|---|---|
| 464 | 3.0 | 9.7 |
| 465 | 3.7 | 8.7 |
| 469 | 3.0 | 9.6 |
| 474 | 3.9 | 9.9 |
| 476 | 4.7 | |
| 477 | 4.8 | 9.9 |
| 478 | 5.0 | 9.6 |
| Mean | 4.08 | 9.52 |
| Standard Deviation | 0.83 | 0.44 |

A similar serological analysis was also performed with respect to those birds which were not challenged with a virulent strain of TRTV, using ten serum samples taken from birds from each of 5 different air spaces of the Mossbank parent breeder flocks (Marshalls Agriculture) at 25 and 41 weeks of age. Table 19 presents the mean antibody titers of these birds from the parent breeder flock.

TABLE 19

Mean Antibody Titers Of Parent Breeder Flock

| house | 25 weeks old (n = 10): Mean | SD | 41 weeks old (n = 10): Mean | SD |
|---|---|---|---|---|
| 4A | 7.60 | 2.57 | 7.39 | 1.72 |
| 5A | 7.51 | 0.81 | 8.27 | 0.87 |
| 3B | 7.44 | 2.55 | 7.29 | 1.50 |
| 4B | 8.16 | 0.67 | 6.64 | 1.46 |
| 5B | 7.34 | 1.81 | 7.17 | 0.98 |

For both the unchallenged vaccinated and the unchallenged negative control birds, blood was collected at ages of 1-day-old and 4, 6, and 8 weeks of age. Table 20 presents this mean antibody titers for the unchallenged birds.

TABLE 20

Mean Antibody Titers For Unchallenged Birds

| | nonvaccinated negative control birds | | | vaccinated birds | | |
|---|---|---|---|---|---|---|
| age | mean | SD | n | mean | SD | n |
| 1-day | 7.23 | 1.32 | 10 | 6.46 | 0.99 | 10 |
| 4 weeks | 3.52 | 0.54 | 38 | 4.38 | 1.86 | 39 |
| 6 weeks | 3.93 | 0.72 | 28 | 4.72 | 1.62 | 27 |
| 8 weeks | 3.54 | 0.75 | 14 | 5.09 | 1.68 | 14 |

For both the challenged vaccinated and the challenged positive control birds, blood was collected 14 days post-challenge for each of the 4-week and the 6-week challenged/ groups. Table 21 presents this mean antibody titers for the challenged birds in these 2 groups.

TABLE 21

| Titers For Challenged Birds At 14 Days PC | | | | | | |
|---|---|---|---|---|---|---|
| | 4-week challenge | | | 6-week challenge | | |
| group | mean | SD (P) | n | mean | SD (P) | n |
| positive control birds | 9.6 | 0.41 (—) | 10 | 9.52 | 0.44 (—) | 13 |
| vaccinated birds | 10.19 | 0.70 (0.031) | 10 | 10.22 | 0.55 (0.001) | 14 |

Individual results were available to support the data presented above in Tables 14-21. Based on the above serological analysis, the following conclusions were made. For both the vaccinated birds and the negative control birds, at an age of 1 day, these birds possessed maternal antibodies (MA) to TRTV. By 4 weeks of age, antibody levels in the negative control birds had dropped to the negative range and remained low throughout the remainder of the experiment. Following in ovo administration with a titer of $10^{3.2}$ $TCID_{50}$ of a vaccine derived from Poulvac® TRT, mean antibody titers remained in the negative range (i.e., below the positive cutoff value of 6.0) but increased with age. At 4, 6, and 8 weeks of age, the vaccinated birds possessed mean antibody titer levels which were statistically significantly higher than those of the negative control birds. From 4 weeks of age, 20% to 22% of the vaccinated birds had positive titers. With respect to the challenged birds, all birds showed seroconversion at 14 days post-challenge. For both the 4-week and the 6-week challenge studies, the mean titers of the vaccinated group were higher than those of the positive control birds and this difference was statistically significant ($P<0.05$).

An analysis of the entirety of Example 4, including the experimentally-obtained measurements, results, and corresponding statistical analysis indicates that in ovo vaccination of maternal-antibody-positive (MA+) commercial broiler eggs at 18 days incubation with a vaccine derived from Poulvac® TRT at a dosage titer of $10^{3.2}$ $TCID_{50}$ per egg did not adversely effect hatchability and provided a reliable, efficient, and efficacious method of vaccine administration. This vaccination also conferred significant protection against challenge with a virulent strain of TRTV at 6 weeks of age—when the clinical signs seen were significantly reduced. There was a degree of protection at 4-weeks of age—however, even in the nonvaccinated positive control birds the clinical signs seen at this time were not very severe. Accordingly, although present, the protection afforded against a challenge at 4-weeks was not statistically significant.

The data presented in this Example 4, in combination with that of Examples 1-3 above, established that chickens are far less susceptible to TRT vaccines. Positive mean antibody titers (above the positive cutoff value of 6.0) were not observed after in ovo vaccination. However, the levels in the vaccinated group were significantly higher than those seen in the negative controls. Approximately one-fifth of the vaccinated birds had positive titers after 4 weeks of age. Therefore, at the time of challenge, overall seroconversion to ELISA levels above 6.0 may not be a good indicator of the protection actually afforded by the in ovo vaccination. Local immunity may play a role in the interaction between the protection induced and the experimentally-determined titers.

Prior to the analysis of Experiments 14 above, it had been postulated that the presence of maternal antibodies would adversely effect the effectiveness of vaccines. Example 4 nonetheless and surprisingly establishes that in ovo administration of a TRT vaccine at a titer of $10^{3.2}$ $TCID_{50}$ per egg was efficacious in reducing clinical TRT disease in chickens that are MA+. Example 4 strengthens and extends the conclusions reached in Example 3 above; namely, that SPF (MA−) chickens which were vaccinated in ovo likewise experienced a reduction of clinical disease.

Example 5

Study of TRT Vaccine in Combination with Other Poultry Vaccines

The following abbreviations are utilized in this study:

AHS: Animal Health Service, Deventer, The Netherlands
BC: Biochek, Gouda, The Netherlands
CVL: Central Veterinary Laboratory, Weybridge, UK
$EID_{50}$: 50% egg infective dose
ELISA: enzyme-linked immunosorbent assay
FAT: fluorescent antibody test
HI: haemagglutination inhibition
IB: infectious bronchitis
IBD: infectious bursal disease
i.m.: intramuscular(ly)
MD: Marek's disease
ND: Newcastle disease
P: probability
$TCID_{50}$: 50% tissue culture infective dose
TRT: turkey rhinotracheitis The following vaccine materials were utilized for this study:

Poulvacc® TRT, batches TR02100 and TR02200, containing $10^{4.1}$ and $10^{4.1}$ $TCID_{50}$ $TCID_{50}$ TRT virus per dose, respectively.

Poulvac® Ovoline ND, batch BB010, containing $10^{3.9}$ $EID_{50}$ ND virus per vial (5000 doses per vial).

Bursamune IN OVO, batch 61640, containing 5000 doses per vial.

Poulvac® Marek HVT lyo, batch 350129, containing MD virus, strain FC126 (1000 doses per vial).

Poulvac® NDW, batches BL03200 and BL04302.

Poulvac® IB Primer, batch CX02301, containing $10^{5.0}$ $EID_{50}$ IB virus, serotypes M41 and D207 (D274 Clone), per dose (1000 doses per vial).

Poulvac® Bursa Plus, batch 62481, containing $10^{3.2}$ $EID_{50}$ IBD virus, strain V877, per vial (2000 doses per vial).

All vaccines, except for Bursamune IN OVO, were supplied by Fort Dodge Animal Health Benelux, Weesp, The Netherlands. Bursamune IN OVO was obtained from Fort Dodge Animal Health, Australia.

Vaccine batches were stored at 0-8° C., protected from light, until the day of use and were used according to the manufacturer's specifications. After reconstitution, the vaccines were used within two hours. The following vaccine dilutions were prepared.

Vaccine dilution for vaccination in-ovo group 1 Poulvac® TRT, batch TR02100, Poulvac® Ovoline ND and Bursamune IN OVO were reconstituted and further diluted in Poulvac® Marek diluent, batch C8109. The final dilution contained one commercial dose of each vaccine in 0.05 ml.

Vaccine dilution for intramuscular (i.m.) vaccination groups 1 and 2 against MD

Poulvac® Marek HVT lyo was reconstituted and further diluted in Poulvac® Marek diluent, batch C8109. The dilution contained one commercial dose per 0.5 ml.

Vaccine dilution for coarse spray vaccination group 1 Poulvac® IB Primer was reconstituted and further diluted in 2.2 litres of demineralized water. The dilution contained one commercial dose per 0.5 ml.

Vaccine dilution for coarse spray vaccination group 2 Poulvac® NDW, batch BL04302, Poulvac® IB Primer, and Poulvac® TRT, batch TR02200, were reconstituted and further diluted in 3 litres of demineralized water. The final dilution contained one commercial dose per 0.5 ml.

Vaccine dilution for vaccination group 2 against IBD in drinking water Three vials Poulvac® Bursa Plus were reconstituted and further diluted in tap water.

Vaccine dilution for vaccination groups 1 and 2 against ND by Atomist spray Poulvac® NDW, batch BL03200 was reconstituted and further diluted in demineralized water until the final dilution contained one commercial dose per 0.5 ml.

14895 commercial eggs of Cobb breed for broiler production, obtained from Pronk, Meppel, The Netherlands, were placed in one incubator located in MUK-5/6 at the test farm of Fort Dodge AHH, Muiden, The Netherlands. All eggs were candied after 17 days of incubation. Non-fertilised eggs or eggs with dead embryos were removed.

6001 Eggs assigned to group 1 were inoculated with 0.05 ml of a dilution containing 1 dose of Poulvac® TRT, Poulvac® Ovoline ND and Bursamune IN OVO per egg after 18 days incubation using an Embrex Inovoject egg injection machine according to the manufacturer's instructions. 6028 Eggs assigned to group 2 were left non-inoculated.

Inoculated (group 1) and non-inoculated (group 2) eggs were further incubated (without turning) until hatching in the incubators 1 and 4, respectively, located at the test farm of Fort Dodge AHH, Muiden, The Netherlands. After hatching, 4452 (inoculated, group 1) and 5248 (non-inoculated, group 2) chicks were included in the study, respectively. The chicks were group-housed on wood shavings in animal facilities located in the same shed at the test farm of Fort Dodge AHH, Muiden, The Netherlands. Chicks of group 1 were housed in MUL-L and chicks of group 2 in MUL-R. All chicks were fed ad libitum with commercial broiler pellet and had free access to drinking water provided in bell drinkers.

The vaccination schedule is shown in Table 22. At one day of age, chicks of group 1 were vaccinated with Poulvac® IB Primer. One commercial dose was administered by coarse spray using a garden sprayer (Gardena) in 0.5 ml per chick. At one day of age, chicks of group 2 were vaccinated with Poulvac® TRT, Poulvac® NDW and Poulvac® IB Primer. One commercial dose of each vaccine was administered by coarse spray in one volume of 0.5 ml per chick, as in group 1. Before coarse spray vaccination, the chicks were placed in chicken boxes and were left therein until 3 hours post-vaccination.

All chicks were vaccinated with Poulvac® Marek HVT lyo, one commercial dose per chick, at one day of age. The vaccine was i.m. applied in the thigh, using a Pullet Injection Gun (Veterinary Supplies, Mijdrecht, The Netherlands) with a pre-set volume of 0.5 ml.

Chicks of group 2 were vaccinated with Poulvac® Bursa Plus, one commercial dose per chick in the drinking water, at 2 weeks of age. The vaccine was distributed in a quantity of water that was consumed within 2 hours. The chicks were deprived of drinking water during 2 hours before the vaccine was administered.

All chicks were vaccinated with Poulvac® NDW at 4 weeks of age. One commercial dose in 0.5 ml per chick was applied by atomiser. Table 22. Vaccination schedule.

TABLE 22

Vaccination schedule.

| Group 1 | Age at vaccination eggs 18 days of incubation | vaccine Poulvac TRT) Poulvac Ovoline ND) Bursamune IN OVO) | application method injection machine |
|---|---|---|---|
| 1 | Chicks 1 day of age | Poulvac IB Primer) Poulvac Marek HVT lyo | coarse spray in chicken box i.m. |
| 2 | Chicks 1 day of age | Poulvac TRT) Poulvac NDW) Poulvac IB Primer) Poulvac Marek HVT lyo | coarse spray in chicken box i.m. |
| 2 | Chicks 2 weeks of age | Poulvac Bursa Plus | drinking water |
| 1 and 2 | Chicks 4 weeks of age | Poulvac NDW | atomiser |

Blood samples were taken from 30 chicks of each group after decapitation at one day of age. Samples of 10 chicks of each group were used for serological tests at AHS. Samples of 10 other chicks of each group were used for serological tests at the Central Veterinary Laboratory, Weybridge, UK (CVL). The remaining 10 samples were used for serological tests at BC. Blood samples were collected from the wing vein up to a maximum number of 24 chicks per group at 2, 3, 4, 5 and 6 weeks of age.

Antibody titres to ND, IB M41 and IB D274 antigens were determined using HI tests. The detection limit of the HI tests corresponds with 2log HI titre=1.0 for ND antigen and with 2log HI titre=3.0 for IB antigens. Geometric mean HI titres were calculated. Antibody titres to TRT and IBD virus were measured using an ELISA method (IDEXX) according to the manufacturer's instructions and mean titres were calculated. These tests were done at AHS.

Antibody titrations to ND, IB, TRT and IBD virus using ELISA methods were done by BC. ELISA antibody titres of 1159 and 834 or above to ND and IB virus, respectively, are regarded positive. Antibody titres to ND (regarded positive at 396 or above) and IB virus were also determined using the IDEXX test kits. Mean titres were calculated using the BC99 software.

The results obtained at AHS and CVL were analyzed statistically. The two groups were compared with respect to antibody titres by means of Student's 2-sided t test. ELISA antibody titres to IBD, TRT and MD were log transformed (log [x+1]) before analysis. The MD measurements $\geqq 1600$ and neg. were replaced by 1600 and 25 in the calculations, respectively. A probability of $P \leqq 0.05$ was considered as a statistically significant difference.

Results: Mean antibody titres to ND, IB, IBD and TRT antigens, determined by AHS and BC, are shown in Tables 23 and 24.

TABLE 23

Mean antibody titres to ND, IB M41, IB D274, IBD and TRT, determined by AHS.

| | | mean 2log HI antibody titre | | | mean ELISA antibody titre | |
|---|---|---|---|---|---|---|
| age | Group | ND | IB M41 | IB D274 | IBD | TRT |
| one day | 1 | 5.4 (n = 10) | 8.0 (n = 10) | 7.9 (n = 10) | 2377 (n = 10) | 4896 (n = 10) |
| | 2 | 5.8 (n = 10) | 8.1 (n = 10) | 7.9 (n = 10) | 3084 (n = 10) | 1628 (n = 10)* |
| 2 weeks, vaccination with Poulvac Bursa Plus (group 2) | | | | | | |
| | 1 | 2.3 (n = 24) | 6.2 (n = 24) | 6.5 (n = 24) | 94 (n = 24) | 509 (n = 24) |
| | 2 | 2.2 (n = 24) | 5.8 (n = 24) | 6.3 (n = 24) | 109 (n = 24) | 371 (n = 24)* |
| 3 weeks | | | | | | |
| | 1 | 2.5 (n = 24) | 5.4 (n = 24) | 5.6 (n = 24) | 51 (n = 24) | 203 (n = 24) |
| | 2 | 1.2 (n = 23)* | 5.4 (n = 20) | 5.4 (n = 23) | 45 (n = 24) | 90 (n = 24)* |
| 4 weeks, vaccination with Poulvac NDW (groups 1 and 2) | | | | | | |
| | 1 | 1.8 (n = 24) | 3.8 (n = 23) | 4.1 (n = 24) | 951 (n = 24) | 76 (n = 23) |
| | 2 | 1.3 (n = 24) | 3.7 (n = 24) | 4.0 (n = 24) | 1196 (n = 24) | 7 (n = 24)* |
| 5 weeks | | | | | | |
| | 1 | 3.6 (n = 24) | 4.6 (n = 21) | 4.9 (n = 21) | 1392 (n = 24) | 426 (n = 24) |
| | 2 | 1.8 (n = 24)* | 4.0 (n = 22) | 4.2 (n = 22) | 1210 (n = 24) | 41 (n = 24)* |
| 6 weeks | | | | | | |
| | 1 | 2.3 (n = 24) | 4.3 (n = 24) | 4.6 (n = 24) | 1907 (n = 24) | 215 (n = 24) |
| | 2 | 3.3 (n = 24)* | 3.7 (n = 24)* | 3.8 (n = 24)* | 1857 (n = 24) | 72 (n = 24) |

*statistically significantly different from group 1 ($P \leqq 0.05$).

TABLE 24

Mean antibody titres to ND, IB, IBD and TRT, determined by BC.

| | | mean ELISA antibody titre | | | |
|---|---|---|---|---|---|
| Age | Group | ND | IB | IBD | TRT |
| one day | 1 | 7309 (n = 10) | 6316 (n = 10) | 4643 (n = 10) | 11144 (n = 10) |
| | 2 | 7087 (n = 10) | 6148 (n = 10) | 4601 (n = 10) | 2594 (n = 10) |
| 2 weeks, vaccination with Poulvac Bursa Plus (group 2) | | | | | |
| | 1 | 1279 (n = 24) | 497 (n = 24) | 399 (n = 24) | 804 (n = 24) |
| | 2 | 1088 (n = 24) | 649 (n = 24) | 400 (n = 24) | 610 (n = 24) |
| 3 weeks | | | | | |
| | 1 | 1934 (n = 24) | 687 (n = 24) | 440 (n = 24) | 316 (n = 24) |
| | 2 | 763 (n = 24) | 718 (n = 24) | 854 (n = 24) | 258 (n = 24) |
| 4 weeks, vaccination with Poulvac NDW (groups 1 and 2) | | | | | |
| | 1 | 924 (n = 24) | 1100 (n = 24) | 5448 (n = 24) | 298 (n = 24) |
| | 2 | 530 (n = 24) | 680 (n = 24) | 6291 (n = 24) | 451 (n = 24) |
| 5 weeks | | | | | |
| | 1 | 2918 (n = 24) | 1041 (n = 24) | 6142 (n = 24) | 483 (n = 24) |
| | 2 | 1604 (n = 24) | 752 (n = 24) | 5948 (n = 24) | 279 (n = 24) |
| 6 weeks | | | | | |
| | 1 | 3074 (n = 24) | 1435 (n = 24) | 6322 (n = 24) | 456 (n = 24) |
| | 2 | 2536 (n = 24) | 2662 (n = 24) | 6801 (n = 24) | 681 (n = 24) |

Mean fat titres to MD virus, representing the mean serum dilution demonstrating specific fluorescence, are shown in Table 25. Statistically significant higher FAT titres were observed in group 2 at 2, 3, and 4 weeks of age, showing a higher immunological response at younger age of the birds.

TABLE 25

Mean FAT titres to MD virus.

| Age | group | no. samples | mean FAT titre to MD virus |
|---|---|---|---|
| one day | 1 | 10 | 880 |
| | 2 | 10 | 940 |
| 2 weeks | 1 | 24 | 66 |
| | 2 | 24 | 175* |
| 3 weeks | 1 | 24 | 172 |
| | 2 | 24 | 612* |
| 4 weeks | 1 | 24 | 369 |
| | 2 | 24 | 823* |
| 5 weeks | 1 | 24 | 950 |
| | 2 | 24 | 877 |
| 6 weeks | 1 | 24 | 1129 |
| | 2 | 24 | 1267 |

*statistically significantly different from group 1 (P ≦ 0.05).

Example 5

Discussion

Chicks in both groups had MA against ND, IB, IBD, TRT and MD virus. A seroresponse to ND and IB was observed after vaccination at one day old. Development of titres to these antigens was within normal ranges in both groups. The second vaccination with Poulvac® NDW induced a seroresponse in both groups. Both groups developed antibody titres to IBD, TRT and MD virus.

In a number of cases, certain differences in antibody titres between groups was observed. Antibody titres to ND were higher in group 1 (chicks hatched from inoculated eggs) in all cases except at 6 weeks of age. Antibody titres to TRT were also higher in group 1 in all cases and these differences were statistically significant except for the difference at 6 weeks of age. The seroresponse to MD was somewhat slower in group 1 but reached the same level as in group 2 at 5 weeks of age. No clear differences between groups in mean antibody titres to IB and IBD antigens were observed. In most instances, the results of the titrations done at BC followed the same pattern as those obtained at AHS, with higher values for the ELISA titres to IBD and TRT. A seroresponse to IBD was shown by the BC test at 3 weeks of age, which is one week before it was shown in the IDEXX test. The BC ELISA test seems more sensitive to measure antibody titres to ND than the HI method. The BC ELISA test showed a more pronounced response to IB virus than the HI method from 3 weeks of age onwards.

In-ovo vaccination of commercial eggs for broiler production with one commercial dose of Poulvac® TRT, Poulvac® Ovoline ND and Bursamune IN OVO after 18 days of incubation followed by vaccination with Poulvac IB Primer and Poulvac® HVT at one day of age is compatible regarding efficacy with vaccination of the hatched chicks with commercial dosages of Poulvac TRT, Poulvac® NDW, Poulvac® IB Primer and Poulvac® Marek HVT lyo on the first day of life and with vaccination with Poulvac® Bursa Plus at 2 weeks of age.

The BC ELISA test kits seems favorable for measuring antibody titre levels to ND, IB, IBD and TRT viral antigens compared to HI tests to ND, IB M41 and IB D274, or IDEXX test kits to IBD or TRT.

Tables 26 through 35 provide additional antibody titre results.

TABLE 26

HI antibody titres to ND virus, determined by AHS.

| age | Group | no. chicks with indicated 2log HI titre to ND virus: 1 | 2 | 3 | 4 | 5 | 6 | 7 | 8 | 9 | Insufficient Serum |
|---|---|---|---|---|---|---|---|---|---|---|---|
| one day | | | | | | | | | | | |
| | 1 | | | | 1 | 5 | 3 | 1 | | | |
| | 2 | | | | 2 | 2 | 2 | 4 | | | |
| 2 weeks | | | | | | | | | | | |
| | 1 | 6 | 12 | 3 | 1 | 1 | | 1 | | | |
| | 2 | 2 | 16 | 6 | | | | | | | |
| 3 weeks | | | | | | | | | | | |
| | 1 | 7 | 7 | 6 | 1 | 2 | | 1 | | | |
| | 2 | 20 | 2 | 1 | | | | | | | 1 |
| 4 weeks | | | | | | | | | | | |
| | 1 | 15 | 4 | 2 | 1 | 1 | 1 | | | | |
| | 2 | 19 | 3 | 1 | 1 | | | | | | |
| 5 weeks | | | | | | | | | | | |
| | 1 | 4 | 3 | 6 | 4 | | 7 | | | | |
| | 2 | 12 | 7 | 4 | 1 | | | | | | |
| 6 weeks | | | | | | | | | | | |
| | 1 | 7 | 7 | 6 | 3 | 1 | | | | | |
| | 2 | 4 | 4 | 4 | 6 | 4 | 2 | | | | |

TABLE 27

HI antibody titres to IB M41 antigen, determined by AHS.

| age | Group | no. chicks with indicated 2log HI titre to IB M41 antigen: 3 | 4 | 5 | 6 | 7 | 8 | 9 | 10 | 11 | Insufficient Serum |
|---|---|---|---|---|---|---|---|---|---|---|---|
| one day | | | | | | | | | | | |
| | 1 | | | | 3 | | 2 | 4 | 1 | | |
| | 2 | | | | | 3 | 5 | 1 | | 1 | |
| 2 weeks | | | | | | | | | | | |
| | 1 | 1 | 3 | 3 | 5 | 8 | 4 | | | | |
| | 2 | | 1 | 7 | 11 | 5 | | | | | |
| 3 weeks | | | | | | | | | | | |
| | 1 | 2 | 2 | 7 | 10 | 3 | | | | | |
| | 2 | 2 | 3 | 3 | 9 | 3 | | | | | 4 |
| 4 weeks | | | | | | | | | | | |
| | 1 | 10 | 9 | 3 | 1 | | | | | | |
| | 2 | 14 | 5 | 4 | | 1 | | | | | |
| 5 weeks | | | | | | | | | | | |
| | 1 | 7 | 3 | 6 | 3 | 1 | 1 | | | | 3 |
| | 2 | 11 | 3 | 6 | 2 | | | | | | 2 |
| 6 weeks | | | | | | | | | | | |
| | 1 | 6 | 10 | 4 | 4 | | | | | | |
| | 2 | 11 | 10 | 2 | 1 | | | | | | |

TABLE 28

HI antibody titres to IB D274 antigen, determined by AHS.

| age | group | no. chicks with indicated 2log HI titre to IB D274 antigen: 3 | 4 | 5 | 6 | 7 | 8 | 9 | 10 | 11 | Insufficient Serum |
|---|---|---|---|---|---|---|---|---|---|---|---|
| one day | | | | | | | | | | | |
| | 1 | | | | 1 | 4 | 2 | 2 | | 1 | |
| | 2 | | | 1 | 2 | 2 | | 3 | 1 | 1 | |
| 2 weeks | | | | | | | | | | | |
| | 1 | | 2 | 3 | 5 | 9 | 5 | | | | |
| | 2 | | | 2 | 12 | 10 | | | | | |
| 3 weeks | | | | | | | | | | | |
| | 1 | | 4 | 5 | 12 | 2 | 1 | | | | |
| | 2 | 1 | 4 | 6 | 8 | 4 | | | | | |

TABLE 28-continued

HI antibody titres to IB D274 antigen, determined by AHS.

| age | group | no. chicks with indicated 2log HI titre to IB D274 antigen: 3 | 4 | 5 | 6 | 7 | 8 | 9 | 10 | 11 | Insufficient Serum |
|---|---|---|---|---|---|---|---|---|---|---|---|
| 4 weeks | | | | | | | | | | | |
| | 1 | 8 | 8 | 6 | 2 | | | | | | |
| | 2 | 10 | 8 | 3 | 2 | 1 | | | | | |
| 5 weeks | | | | | | | | | | | |
| | 1 | 7 | 2 | 3 | 6 | 1 | 2 | | | | 3 |
| | 2 | 7 | 6 | 6 | 3 | | | | | | 2 |
| 6 weeks | | | | | | | | | | | |
| | 1 | 5 | 6 | 9 | 1 | 3 | | | | | |
| | 2 | 12 | 6 | 5 | 1 | | | | | | |

TABLE 29

Individual ELISA antibody titres to IBD virus, determined by AHS.
ELISA antibody titre to IBD virus per group at various ages

| 1 day group 1 | 1 day group 2 | 2 weeks group 1 | 2 weeks group 2 | 3 weeks group 1 | 3 weeks group 2 | 4 weeks group 1 | 4 weeks group 2 | 5 weeks group 1 | 5 weeks group 2 | 6 weeks group 1 | 6 weeks group 2 |
|---|---|---|---|---|---|---|---|---|---|---|---|
| 1124 | 531 | 0 | 0 | 0 | 0 | 38 | 33 | 567 | 342 | 564 | 644 |
| 1547 | 1927 | 0 | 2 | 0 | 0 | 174 | 57 | 648 | 368 | 826 | 809 |
| 1799 | 2076 | 2 | 25 | 0 | 0 | 299 | 299 | 648 | 653 | 1038 | 1004 |
| 2388 | 2584 | 8 | 38 | 0 | 0 | 570 | 325 | 954 | 907 | 1132 | 1012 |
| 2421 | 2989 | 8 | 38 | 0 | 0 | 577 | 564 | 1005 | 986 | 1279 | 1462 |
| 2453 | 3355 | 8 | 51 | 0 | 0 | 637 | 660 | 1024 | 1119 | 1314 | 1497 |
| 2529 | 3466 | 13 | 57 | 0 | 0 | 721 | 690 | 1084 | 1167 | 1418 | 1524 |
| 2704 | 4096 | 13 | 57 | 0 | 0 | 729 | 744 | 1114 | 1339 | 1550 | 1533 |
| 3199 | 4550 | 19 | 64 | 0 | 0 | 751 | 886 | 1128 | 1339 | 1683 | 1674 |
| 3600 | 5262 | 25 | 64 | 0 | 0 | 805 | 919 | 1152 | 1378 | 1701 | 1728 |
| | | 32 | 77 | 0 | 0 | 867 | 984 | 1183 | 1388 | 1719 | 1844 |
| | | 44 | 77 | 3 | 0 | 883 | 1031 | 1243 | 1456 | 1871 | 1853 |
| | | 44 | 111 | 15 | 3 | 929 | 1084 | 1247 | 1460 | 1888 | 1897 |
| | | 51 | 118 | 19 | 3 | 953 | 1141 | 1257 | 1577 | 1969 | 1987 |
| | | 57 | 118 | 57 | 8 | 968 | 1185 | 1538 | 1577 | 1987 | 1906 |
| | | 105 | 125 | 65 | 15 | 976 | 1261 | 1716 | 1972 | 2078 | 1996 |
| | | 118 | 125 | 80 | 15 | 984 | 1269 | 1762 | 1987 | 2195 | 2014 |
| | | 147 | 161 | 104 | 28 | 1000 | 1430 | 1767 | 448 | 2250 | 2123 |
| | | 161 | 168 | 137 | 28 | 1078 | 1690 | 1873 | 613 | 2387 | 2214 |
| | | 175 | 182 | 137 | 28 | 1567 | 1808 | 1875 | 1179 | 2432 | 2250 |
| | | 234 | 197 | 137 | 113 | 1681 | 2009 | 1903 | 1217 | 2885 | 2314 |
| | | 271 | 212 | 146 | 182 | 1772 | 2326 | 1993 | 1281 | 2968 | 2497 |
| | | 278 | 234 | 154 | 214 | 1862 | 2362 | 2062 | 1308 | 3033 | 3005 |
| | | 446 | 316 | 162 | 434 | 2011 | 3951 | 2654 | 1981 | 3616 | 3787 |

TABLE 30

Individual ELISA antibody titres to TRT virus, determined by AHS.
ELISA antibody titre to TRT virus per group at various ages

| 1 day group 1 | 1 day group 2 | 2 weeks group 1 | 2 weeks group 2 | 3 weeks group 1 | 3 weeks group 2 | 4 weeks group 1 | 4 weeks group 2 | 5 weeks group 1 | 5 weeks group 2 | 6 weeks group 1 | 6 weeks group 2 |
|---|---|---|---|---|---|---|---|---|---|---|---|
| 6167 | 1627 | 465 | 0 | 0 | 1134 | 85 | 46 | 316 | 0 | 0 | 0 |
| 5889 | 2936 | 0 | 0 | 0 | 0 | 85 | 0 | 0 | 0 | 0 | 0 |
| 6096 | 4819 | 371 | 602 | 0 | 0 | 0 | 0 | 0 | 0 | 19 | 0 |
| 3542 | 1457 | 65 | 0 | 0 | 0 | 0 | 0 | 0 | 0 | 709 | 0 |
| 1036 | 1853 | 0 | 1686 | 0 | 0 | 153 | 0 | 342 | 0 | 0 | 0 |
| 3305 | 681 | 19 | 0 | 0 | 0 | 153 | 0 | 0 | 0 | 380 | 337 |

TABLE 30-continued

Individual ELISA antibody titres to TRT virus, determined by AHS.
ELISA antibody titre to TRT virus per group at various ages

| 1 day | | 2 weeks | | 3 weeks | | 4 weeks | | 5 weeks | | 6 weeks | |
|---|---|---|---|---|---|---|---|---|---|---|---|
| group 1 | group 2 | group 1 | group 2 | group 1 | group 2 | group 1 | group 2 | group 1 | group 2 | group 1 | group 2 |
| 1784 | 295 | 371 | 0 | 0 | 0 | 0 | 0 | 342 | 0 | 204 | 161 |
| 7540 | 1332 | 2504 | 0 | 65 | 414 | 0 | 0 | 0 | 931 | 342 | 69 |
| 3899 | 840 | 227 | 740 | 241 | 0 | 0 | 0 | 781 | 0 | 123 | 0 |
| 9698 | 442 | 711 | 1612 | 346 | 0 | 383 | 0 | 19 | 0 | 0 | 0 |
| | | 346 | 0 | 213 | 0 | 55 | 0 | 275 | 0 | 881 | 0 |
| | | 565 | 0 | 0 | 376 | 0 | 0 | 709 | 0 | 0 | 69 |
| | | 0 | 0 | 0 | 0 | 0 | 0 | 289 | 0 | 0 | 500 |
| | | 1876 | 0 | 465 | 0 | 0 | 0 | 380 | 0 | 0 | 0 |
| | | 0 | 0 | 0 | 0 | 0 | 126 | 106 | 0 | 0 | 0 |
| | | 103 | 368 | 0 | 0 | 0 | 0 | 45 | 0 | 262 | 0 |
| | | 0 | 1669 | 442 | 0 | 0 | 0 | 0 | 0 | 1669 | 0 |
| | | 840 | 289 | 442 | 0 | 0 | 0 | 2620 | 0 | 0 | 0 |
| | | 120 | 0 | 499 | 0 | 0 | 0 | 1289 | 0 | 0 | 0 |
| | | 0 | 881 | 741 | 0 | 0 | 0 | 761 | 46 | 219 | 0 |
| | | 499 | 1063 | 1008 | 89 | 169 | 0 | 852 | 0 | 204 | 365 |
| | | 1161 | 0 | 227 | 0 | 282 | 0 | 781 | 0 | 0 | 89 |
| | | 1547 | 0 | 103 | 144 | 454 | 0 | 204 | 0 | 0 | 144 |
| | | 430 | 0 | 85 | 0 | 0 | 0 | 123 | 0 | 140 | 0 |

TABLE 31

Individual FAT titres to MD virus, determined at CVL.
FAT titres to MD virus per group at various ages

| 1 day of age | | 2 weeks of age | | 3 weeks of age | | 4 weeks of age | | 5 weeks of age | | 6 weeks of age | |
|---|---|---|---|---|---|---|---|---|---|---|---|
| group 1 | group 2 | group 1 | group 2 | group 1 | group 2 | group 1 | group 2 | group 1 | group 2 | group 1 | group 2 |
| 800 | ≧1600 | 100 | 200 | 100 | 400 | 100 | ≧1600 | 800 | 200 | 800 | 800 |
| 400 | 800 | 50 | 400 | neg. | 400 | 200 | 800 | 800 | 50 | ≧1600 | 800 |
| ≧1600 | 800 | 50 | 200 | 100 | 200 | 100 | 200 | 400 | ≧1600 | 800 | 800 |
| 800 | 800 | neg. | 400 | 400 | ≧1600 | 200 | ≧1600 | 800 | ≧1600 | 400 | 800 |
| 400 | 200 | 100 | 400 | 50 | 400 | 100 | 400 | 200 | 400 | 800 | 800 |
| 800 | ≧1600 | 100 | 200 | 50 | 800 | 800 | 800 | ≧1600 | ≧1600 | 800 | ≧1600 |
| 400 | 400 | 100 | 100 | 50 | 800 | 200 | ≧1600 | 800 | 400 | 800 | ≧1600 |
| ≧1600 | ≧1600 | 100 | 100 | 50 | ≧1600 | 50 | 800 | 400 | 800 | ≧1600 | ≧1600 |
| ≧1600 | 800 | 50 | 50 | 400 | 800 | 800 | 800 | 400 | 800 | ≧1600 | 800 |
| 400 | 800 | 50 | 200 | 400 | 400 | 100 | 800 | ≧1600 | 800 | 800 | 800 |
| | | 50 | 100 | 100 | 800 | 400 | 100 | 200 | ≧1600 | ≧1600 | 800 |
| | | 100 | 200 | 200 | 200 | 50 | 400 | ≧1600 | 400 | ≧1600 | ≧1600 |
| | | 50 | 100 | 400 | 100 | 100 | ≧1600 | 800 | 800 | ≧1600 | 800 |
| | | 50 | 200 | 200 | ≧1600 | 800 | 800 | ≧1600 | 800 | ≧1600 | 800 |
| | | 50 | 200 | 50 | 400 | 100 | ≧1600 | ≧1600 | 800 | ≧1600 | ≧1600 |
| | | 100 | 200 | 400 | 200 | 100 | 200 | 400 | ≧1600 | 400 | ≧1600 |
| | | 100 | 200 | 200 | 200 | 200 | 400 | ≧1600 | 800 | ≧1600 | ≧1600 |
| | | 50 | 200 | 100 | 200 | 800 | ≧1600 | 800 | ≧1600 | 400 | ≧1600 |
| | | 50 | 50 | 200 | ≧1600 | 400 | 400 | 400 | 400 | ≧1600 | ≧1600 |
| | | 100 | 100 | 100 | 400 | ≧1600 | 800 | 800 | 800 | 100 | ≧1600 |
| | | 50 | 100 | 200 | 200 | 400 | 50 | 400 | 400 | ≧1600 | ≧1600 |
| | | neg. | 100 | 200 | 200 | 400 | 400 | ≧1600 | ≧1600 | 200 | ≧1600 |
| | | 50 | 100 | 50 | 400 | 50 | ≧1600 | ≧1600 | 800 | ≧1600 | ≧1600 |
| | | neg. | 100 | 100 | 800 | 800 | 400 | ≧1600 | 400 | ≧1600 | ≧1600 |

TABLE 32

Individual ELISA antibody titres to ND virus, determined by BC.
ELISA antibody titre to ND virus per group at various ages

| 1 day | | 2 weeks | | 3 weeks | | 4 weeks | | 5 weeks | | 6 weeks | |
|---|---|---|---|---|---|---|---|---|---|---|---|
| group 1 | group 2 | group 1 | group 2 | group 1 | group 2 | group 1 | group 2 | group 1 | group 2 | group 1 | group 2 |
| 6742 | 6546 | 901 | 1126 | 2507 | 258 | 1338 | 215 | 705 | 1563 | 3275 | 818 |
| 9414 | 8225 | 454 | 550 | 490 | 175 | 500 | 175 | 1954 | 351 | 543 | 4924 |
| 7434 | 6129 | 1689 | 576 | 245 | 175 | 179 | 2169 | 4934 | 6719 | 9252 | 377 |
| 10709 | 10884 | 1123 | 384 | 6093 | 199 | 262 | 235 | 1172 | 596 | 434 | 1623 |

TABLE 32-continued

Individual ELISA antibody titres to ND virus, determined by BC.
ELISA antibody titre to ND virus per group at various ages

| 1 day | | 2 weeks | | 3 weeks | | 4 weeks | | 5 weeks | | 6 weeks | |
|---|---|---|---|---|---|---|---|---|---|---|---|
| group 1 | group 2 | group 1 | group 2 | group 1 | group 2 | group 1 | group 2 | group 1 | group 2 | group 1 | group 2 |
| 5639 | 7348 | 1808 | 977 | 2278 | 2202 | 818 | 149 | 5709 | 1606 | 1427 | 1225 |
| 1874 | 5096 | 864 | 1185 | 73 | 182 | 162 | 235 | 1964 | 1682 | 2010 | 9378 |
| 9248 | 9033 | 1152 | 242 | 1957 | 1252 | 520 | 894 | 3457 | 2477 | 4477 | 1401 |
| 6510 | 4179 | 1199 | 1652 | 5828 | 325 | 401 | 702 | 2119 | 285 | 4076 | 818 |
| 7530 | 4997 | 735 | 801 | 215 | 225 | 5030 | 1960 | 3695 | 394 | 3623 | 3265 |
| 7990 | 8434 | 460 | 2477 | 209 | 149 | 2179 | 242 | 1864 | 801 | 3858 | 2374 |
| | | 1116 | 1010 | 5768 | 199 | 30 | 149 | 3176 | 242 | 2536 | 6990 |
| | | 1427 | 1785 | 126 | 4503 | 1533 | 182 | 1334 | 3884 | 586 | 791 |
| | | 1132 | 1652 | 2745 | 967 | 1063 | 1543 | 9305 | 1046 | 1136 | 884 |
| | | 1921 | 669 | 245 | 626 | 901 | 818 | 6090 | 2308 | 1079 | 149 |
| | | 752 | 775 | 215 | 225 | 871 | 50 | 222 | 4060 | 3192 | 139 |
| | | 1457 | 1669 | 639 | 566 | 745 | 318 | 3146 | 623 | 3291 | 3146 |
| | | 656 | 1099 | 1927 | 325 | 172 | 268 | 4222 | 1096 | 5205 | 3053 |
| | | 1073 | 1709 | 113 | 199 | 1182 | 182 | 1179 | 977 | 4149 | 944 |
| | | 3729 | 626 | 7477 | 242 | 1301 | 50 | 1079 | 437 | 8639 | 5305 |
| | | 656 | 583 | 2070 | 132 | 66 | 450 | 616 | 1334 | 5679 | 937 |
| | | 2715 | 917 | 447 | 242 | 179 | 460 | 6364 | 1470 | 2010 | 5424 |
| | | 983 | 993 | 3997 | 318 | 371 | 182 | 2073 | 877 | 1589 | 2374 |
| | | 2344 | 1093 | 430 | 325 | 96 | 126 | 3566 | 123 | 871 | 4467 |
| | | 358 | 1553 | 321 | 4295 | 2285 | 977 | 86 | 3536 | 851 | 63 |

TABLE 33

Individual ELISA antibody titres to IB virus, determined by BC.
ELISA antibody titre to IB virus per group at various ages

| 1 day | | 2 weeks | | 3 weeks | | 4 weeks | | 5 weeks | | 6 weeks | |
|---|---|---|---|---|---|---|---|---|---|---|---|
| group 1 | group 2 | group 1 | group 2 | group 1 | group 2 | group 1 | group 2 | group 1 | group 2 | group 1 | group 2 |
| 3606 | 4019 | 609 | 700 | 671 | 504 | 496 | 354 | 1401 | 113 | 484 | 2230 |
| 8858 | 7858 | 71 | 179 | 496 | 629 | 233 | 329 | 4331 | 1071 | 375 | 338 |
| 8041 | 10238 | 671 | 629 | 671 | 434 | 596 | 434 | 1342 | 1784 | 442 | 538 |
| 7254 | 7199 | 171 | 296 | 321 | 308 | 233 | 225 | 513 | 263 | 171 | 3152 |
| 5386 | 6366 | 684 | 1105 | 221 | 1080 | 1296 | 179 | 825 | 338 | 4715 | 834 |
| 8458 | 3231 | 321 | 388 | 271 | 271 | 2639 | 746 | 267 | 438 | 484 | 634 |
| 4206 | 8296 | 896 | 504 | 521 | 700 | 196 | 1209 | 1863 | 1284 | 375 | 8075 |
| 3177 | 2364 | 534 | 1059 | 784 | 354 | 1751 | 1034 | 592 | 475 | 7212 | 1547 |
| 8267 | 6620 | 384 | 342 | 846 | 296 | 3039 | 1151 | 1384 | 163 | 117 | 3539 |
| 5911 | 5290 | 158 | 688 | 721 | 1255 | 1034 | 571 | 429 | 488 | 1276 | 6257 |
| | | 634 | 363 | 258 | 850 | 271 | 1601 | 742 | 1109 | 909 | 1372 |
| | | 984 | 988 | 959 | 1000 | 971 | 271 | 1984 | 475 | 5603 | 7141 |
| | | 521 | 667 | 521 | 2168 | 2526 | 988 | 1251 | 2943 | 1042 | 1684 |
| | | 496 | 817 | 258 | 467 | 884 | 342 | 742 | 1346 | 934 | 288 |
| | | 434 | 642 | 371 | 780 | 634 | 1255 | 975 | 1672 | 484 | 1109 |
| | | 521 | 467 | 333 | 688 | 884 | 446 | 1793 | 1447 | 3460 | 1409 |
| | | 384 | 780 | 1547 | 504 | 2289 | 780 | 346 | 200 | 1888 | 4786 |
| | | 796 | 1392 | 1676 | 513 | 308 | 192 | 688 | 659 | 1984 | 1868 |
| | | 183 | 1255 | 233 | 388 | 1184 | 1000 | 567 | 250 | 308 | 859 |
| | | 1109 | 563 | 1184 | 296 | 671 | 805 | 333 | 350 | 1342 | 1034 |
| | | 271 | 434 | 846 | 780 | 1713 | 133 | 525 | 450 | 158 | 5920 |
| | | 296 | 342 | 221 | 513 | 584 | 513 | 1492 | 375 | 196 | 3139 |
| | | 371 | 513 | 1009 | 1776 | 596 | 805 | 363 | 188 | 225 | 5619 |
| | | 434 | 467 | 1559 | 667 | 1372 | 967 | 238 | 175 | 267 | 513 |

TABLE 34

Individual ELISA antibody titres to IBD virus, determined by BC.
ELISA antibody titre to IBD virus per group at various ages

| 1 day | | 2 weeks | | 3 weeks | | 4 weeks | | 5 weeks | | 6 weeks | |
|---|---|---|---|---|---|---|---|---|---|---|---|
| group 1 | group 2 | group 1 | group 2 | group 1 | group 2 | group 1 | group 2 | group 1 | group 2 | group 1 | group 2 |
| 4992 | 3837 | 352 | 674 | 129 | 166 | 8581 | 184 | 5384 | 7522 | 8305 | 6358 |
| 6396 | 3265 | 215 | 436 | 33 | 115 | 9353 | 7700 | 4798 | 6419 | 4698 | 7756 |
| 5302 | 4215 | 129 | 352 | 76 | 2558 | 3938 | 9419 | 5133 | 12583 | 7539 | 7472 |

TABLE 34-continued

Individual ELISA antibody titres to IBD virus, determined by BC.
ELISA antibody titre to IBD virus per group at various ages

| 1 day | | 2 weeks | | 3 weeks | | 4 weeks | | 5 weeks | | 6 weeks | |
|---|---|---|---|---|---|---|---|---|---|---|---|
| group 1 | group 2 | group 1 | group 2 | group 1 | group 2 | group 1 | group 2 | group 1 | group 2 | group 1 | group 2 |
| 8986 | 7267 | 730 | 45 | 26 | 29 | 1071 | 11617 | 4971 | 4881 | 7152 | 13687 |
| 2112 | 5817 | 926 | 528 | 50 | 100 | 59 | 8172 | 6510 | 3848 | 4612 | 5131 |
| 1829 | 5150 | 582 | 511 | 8044 | 174 | 121 | 4568 | 7488 | 7006 | 5047 | 5850 |
| 7548 | 3613 | 687 | 192 | 76 | 2188 | 3574 | 4800 | 11164 | 5825 | 5373 | 7140 |
| 1970 | 3624 | 644 | 769 | 186 | 158 | 2786 | 9591 | 4971 | 4383 | 7410 | 6833 |
| 3898 | 2243 | 323 | 174 | 352 | 201 | 5652 | 4340 | 5762 | 8615 | 3090 | 5946 |
| 3400 | 6978 | 76 | 1088 | 149 | 115 | 7776 | 6419 | 8829 | 333 | 7023 | 8192 |
| | | 323 | 133 | 26 | 6777 | 7469 | 8866 | 3925 | 6225 | 8818 | 9620 |
| | | 121 | 606 | 79 | 3455 | 9341 | 6336 | 5095 | 4822 | 7435 | 6261 |
| | | 129 | 380 | 26 | 100 | 938 | 6992 | 6947 | 9934 | 3450 | 5789 |
| | | 323 | 473 | 79 | 29 | 10310 | 5289 | 5825 | 5191 | 5398 | 2334 |
| | | 50 | 462 | 94 | 45 | 551 | 5474 | 5436 | 6688 | 8424 | 3592 |
| | | 404 | 316 | 102 | 108 | 4595 | 7435 | 4389 | 7533 | 7295 | 4868 |
| | | 243 | 380 | 264 | 93 | 9600 | 5828 | 5248 | 6627 | 6156 | 5523 |
| | | 344 | 325 | 18 | 38 | 8365 | 4090 | 5674 | 7006 | 8073 | 6128 |
| | | 753 | 52 | 50 | 29 | 9069 | 6491 | 9992 | 5861 | 5185 | 10466 |
| | | 215 | 209 | 205 | 68 | 5368 | 6444 | 6446 | 6103 | 6372 | 6297 |
| | | 571 | 235 | 94 | 115 | 2714 | 11605 | 5839 | 3893 | 5811 | 8840 |
| | | 139 | 425 | 79 | 2 | 5562 | 2047 | 5523 | 5047 | 6588 | 6945 |
| | | 861 | 262 | 112 | 3703 | 5781 | 2755 | 5471 | 2953 | 6065 | 7104 |
| | | 425 | 568 | 205 | 133 | 8177 | 4523 | 6599 | 3466 | 6421 | 5095 |

TABLE 35

Individual ELISA antibody titres to TRT virus, determined by BC.
ELISA antibody titre to TRT virus per group at various ages

| 1 day | | 2 weeks | | 3 weeks | | 4 weeks | | 5 weeks | | 6 weeks | |
|---|---|---|---|---|---|---|---|---|---|---|---|
| group 1 | group 2 | group 1 | group 2 | group 1 | group 2 | group 1 | group 2 | group 1 | group 2 | group 1 | group 2 |
| 14811 | 1295 | 983 | 179 | 560 | 371 | 821 | 636 | 258 | 258 | 33 | 507 |
| 18017 | 3530 | 99 | 66 | 195 | 46 | 225 | 248 | 344 | 354 | 215 | 583 |
| 17444 | 6109 | 368 | 1334 | 99 | 401 | 238 | 513 | 460 | 497 | 517 | 1099 |
| 6566 | 5815 | 298 | 103 | 427 | 103 | 268 | 136 | 248 | 172 | 536 | 2023 |
| 19653 | 3338 | 99 | 2990 | 99 | 56 | 195 | 159 | 828 | 66 | 149 | 646 |
| 2626 | 1854 | 99 | 169 | 722 | 103 | 17 | 103 | 397 | 76 | 53 | 583 |
| 6285 | 288 | 146 | 219 | 56 | 136 | 99 | 401 | 560 | 291 | 129 | 411 |
| 1325 | 1162 | 4086 | 248 | 338 | 656 | 166 | 2119 | 119 | 76 | 20 | 497 |
| 7152 | 1467 | 447 | 626 | 540 | 169 | 318 | 626 | 86 | 225 | 387 | 119 |
| 17563 | 1083 | 470 | 1844 | 288 | 46 | 530 | 921 | 225 | 732 | 440 | 1281 |
| | | 480 | 209 | 166 | 483 | 407 | 533 | 685 | 593 | 1729 | 884 |
| | | 417 | 788 | 56 | 798 | 983 | 705 | 1609 | 205 | 526 | 1099 |
| | | 99 | 56 | 99 | 474 | 146 | 298 | 685 | 507 | 387 | 689 |
| | | 4460 | 103 | 629 | 103 | 99 | 7 | 291 | 368 | 656 | 152 |
| | | 99 | 103 | 99 | 7 | 579 | 228 | 106 | 195 | 106 | 646 |
| | | 156 | 877 | 298 | 331 | 510 | 411 | 20 | 109 | 20 | 517 |
| | | 447 | 228 | 540 | 106 | 407 | 169 | 387 | 109 | 1556 | 430 |
| | | 1132 | 513 | 268 | 66 | 175 | 563 | 987 | 464 | 924 | 550 |
| | | 348 | 381 | 136 | 533 | 288 | 411 | 1278 | 421 | 235 | 656 |
| | | 96 | 1083 | 679 | 103 | 298 | 381 | 656 | 368 | 772 | 1023 |
| | | 530 | 868 | 649 | 126 | 17 | 666 | 546 | 205 | 934 | 689 |
| | | 1146 | 17 | 99 | 103 | 99 | 103 | 526 | 195 | 33 | 626 |
| | | 2083 | 321 | 156 | 778 | 99 | 228 | 33 | 109 | 546 | 517 |
| | | 712 | 1305 | 397 | 96 | 166 | 258 | 258 | 109 | 53 | 109 |

Although the present invention has been described above in considerable detail, applicants desire the full extent of patent protection possible as defined and determined by the claims herein set forth, with reference to the above teachings but not limited to any particularly disclosed example, and in all events, consistent with the widest possible scope of the claims consistent with the spirit and scope of this application.

What is claimed is:

1. A method for protecting an avian host from turkey rhinotracheitis (TRT), turkey rhinotracheitis-related (TRT-related) respiratory distress or Swollen Head Syndrome-related (SHS-related) respiratory distress comprising administering a vaccine in ovo to a fertile egg containing an embryo of the avian host, said vaccine consisting essentially of an immunogenically-effective amount of a live, attenuated strain of turkey rhinotracheitis virus in the approximate range of from about $10^{3.2}$ $TCID_{50}$ per egg to about $10^{5.5}$ $TCID_{50}$ per egg, wherein said vaccine is administered on or before day 24 of incubation and said vaccine is safe upon administration to the egg with respect to hatchability and mortality.

2. The method of claim 1, wherein said immunogenically-effective amount is administered in a suitable vehicle of approximately 0.05 to 0.1 ml per egg.

3. The method of claim 2, wherein the immunogenically-effective amount is about $10^{3.2}$ $TCID_{50}$ per egg.

4. The method of claim 2, wherein the immunogenically-effective amount is about $10^{4.2}$ $TCID_{50}$ per egg.

5. The method of claim 1, wherein said avian host is a turkey or chicken embryo.

6. The method of claim 5, wherein said administration occurs on approximately day 18 of incubation (chicken) or approximately day 24 of incubation (turkey).

7. The method of claim 3, wherein the avian host is either a turkey or a chicken embryo.

8. The method of claim 7, wherein the avian host is a turkey embryo.

9. The method of claim 7, wherein the avian host is a chicken embryo.

* * * * *